(12) United States Patent
Jiang

(10) Patent No.: US 9,676,744 B2
(45) Date of Patent: Jun. 13, 2017

(54) LONG-CHAIN CARBOXYCHROMANOLS AND ANALOGS FOR USE AS ANTI-INFLAMMATORY AGENTS

(71) Applicant: PURDUE RESEARCH FOUNDATION, West Lafayette, IN (US)

(72) Inventor: Qing Jiang, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 0 days.

(21) Appl. No.: 14/472,799

(22) Filed: Aug. 29, 2014

(65) Prior Publication Data

US 2015/0073044 A1    Mar. 12, 2015

Related U.S. Application Data

(63) Continuation-in-part of application No. 13/119,737, filed as application No. PCT/US2009/057293 on Sep. 17, 2009, now Pat. No. 8,822,529.

(60) Provisional application No. 61/098,357, filed on Sep. 19, 2008.

(51) Int. Cl.
    *C07D 311/72*      (2006.01)
    *A61K 31/353*      (2006.01)
    *A61K 31/343*      (2006.01)
    *A61K 31/12*      (2006.01)

(52) U.S. Cl.
    CPC ............ *C07D 311/72* (2013.01); *A61K 31/12* (2013.01); *A61K 31/343* (2013.01); *A61K 31/353* (2013.01)

(58) Field of Classification Search
    CPC .... C07D 311/72; A61K 31/353; A61K 31/12; A61K 31/343
    USPC .................................................. 514/456, 557
    See application file for complete search history.

(56) References Cited

U.S. PATENT DOCUMENTS

| | | | |
|---|---|---|---|
| 5,891,924 A * | 4/1999 | Aggarwal | ............. 514/679 |
| 6,242,479 B1 | 6/2001 | Wechter | |
| 6,350,776 B1 | 2/2002 | Azzi | |
| 6,410,589 B2 | 6/2002 | Wechter | |
| 6,982,282 B2 | 1/2006 | Lambert et al. | |
| 2003/0144219 A1 | 7/2003 | Phinny et al. | |
| 2005/0239876 A1 | 10/2005 | Ames et al. | |
| 2007/0105957 A1 | 5/2007 | Chilton | |

OTHER PUBLICATIONS

The Alpha-Tocopherol, B. C. C. P. S. G. (1994) The effect of vitamin E and beta carotene on the incidence of lung cancer and other cancers in male smokers. The New England journal of medicine 330, 7.
Aronoff, D. M. et al. (2003) J Phannacol Exp Ther 304, 589-595.
Balkwill, F. et al. (2001) Lancet 357, 539-545.
Belardelli, F. (1995) Apmis 103, 161-179.
Berge, S.M., et al., Journal of Pharmaceutical Sciences, vol. 66, No. 1, Jan. 1977.
Bhattacharyya, D. K. et al. (1996) JBiol Chem 271, 2179-2184.
Birringer, M. et al. (2002) J Nutr 132, 3113-3118.
Boutaud, 0. et al. (2002) Proc Nad Acad Sci USA 99, 7130-7135.
Chung et al. (2003) J Nutr 133, 528-532.
Coussens, L. M. et al. (2002) Nature 420, 860-867.
Curcumin Ointment Formulations; Internal journal of Pharmaceutical compounding vol. 1 No. 6 Nov./Dec. 1997 p. 409.
Dubois, R. N. et al. (1998) FasebJ 12, 1063-1073.
Feuerstein, G. et al. (1987) Leukotrienes in health and disease. Faseb J1, 186-192.
Fulton, A. M. et al.(2006) Cancer Res 66, 9794-9797.
Giovannucci, E. et al. (1995) N Engl J Med 333, 609-614.
Guan et al. (2012) Cancer Prey Res (Phila). Apr. 2012;5(4):644-54.
Gupta, R. A. et al. (2001) Nature reviews 1, 11-21.
Gupta, S. et al. (2001) Cancer 91, 737-743.
Gupta, R. A. et al. (2001) Nat Rev Cancer 1, 1-2 1.
Himmelfarb, J. et al. (2003) Kidney Int 64, 978-991.
Ihara et al. (2007) Journal of pharmacological sciences 103, 24-32.
Jacoby et al. (2000) Cancer Res 60, 50405044.
Jiang, Q. et al. (2000) Prac Natl Acad Sci USA 97, 11494-11499.
Jiang, Q. et al. (2001) Am J Clin Nutr 74,714-722.
Jiang, Q. et al. (2002) Free Radic Brat Med 33, 1534-1542.
Jiang, Q. et al. (2003) Faseb J 17, 816-822.
Jiang, Q. et al. (2004) Proc Nall Acad Sci USA 101, 17825-17830.
Jiang, Q. et al. (2007) J Lipid Res 48, 1221-1230.
Jiang, Qing, et al. (2007) J. Lipid Research, vol. 48, No. 5, pp. 1-19.
Kawamori et al. (1998) Cancer Res 58, 409-412.
Klein et al. (2011) JAMA: Journal of the American Medical Association 306, 15491556.
Kurie, J. M and Dubois, R. N. (2001) Olin Cancer Res 7, 2608-261.
Kurumbail, R. G. et al. (2001) CuiT Opin StructBiol 11, 752-760.
Levy, G. N. (1997) Faseb J 11, 234-247.
Libby, P. (2002) Nature 420, 868-874.
Libby, P. et al. (2002) Circulation 105, 1135-1143.
Lippman et al. (2009) JAMA : the journal of the American Medical Association 301, 39-51.
Lorenz, H. M. et al. (2002) Arthritis Res 4, S17-24.
Mancini, J. A. et al. (1995) JBiol Chem 270, 29372-29377.
Marnett, L. J. et al. (1999) Trends Pharmacol Sci 20, 465-469.
Mazzon, E. et al. (2006) Shock 25, 377-383.
McCormick, C. C. & Parker, R. S. (2004) JNutr 134, 3335-3342.
McGeer, P. L. et al. (2001) Neurobiol Aging 22, 799-809.
McLaughlin, P. J. & Weihrauch, J. L. (1979) JAm Diet Assoc 75, 647-665.
Melstrom et al. (2008) Clin Cancer Res 14, 6525-6530.

(Continued)

*Primary Examiner* — Jennifer M Kim
(74) *Attorney, Agent, or Firm* — Purdue Research Foundation; Yonghao Hou

(57) ABSTRACT

Long-chain carboxychromanol compounds useful for treating conditions associated with the need to inhibit cyclooxygenase-1, cyclooxygenase-2, and/or 5-lipoxygenase, and pharmaceutical formulations containing the compounds are provided herein.

5 Claims, 11 Drawing Sheets

(56) References Cited

OTHER PUBLICATIONS

Mitchell, J. A. et al. (1997) Mol Phannacol 51, 907-912.
O'Leary, K. A. et al. (2004) Mutat Res 551, 245-254.
Parker, R. S. et al. (2000) Biochem Biophys Res Commun 277, 531-534.
PCT International Preliminary Report on Patentability for PCT/US2009/057293, completed Mar. 31, 2011.
PCT International Search Report/Written Opinion for PCT/US2009/057293, completed Oct. 21, 2009.
Perry, V. H., Cunningham, C., & Holmes, C. (2007) Nat Rev Immunol 7, 161-167.
Reddy et al. (2000) Cancer Res 60, 293-297.
Reiter, E. et al. (2007) Mol Aspects Med Jan. 11; [Epub ahead of print].
Remington: The Science and Practice of Pharmacy (A. Gennaro, et al., eds., 19th ed., Mack Publishing Co, 1995).
Rieke, C. J. et al. (1999) JBiol Chem 274, 17109-17114.
Router, C. A. & Mamett, L. J. (2003) Chem Rev 143, 2239-2304.
Samad, T. A. et al. (2001) Nature 410, 471-475.
Schonbeck, U. et al. (1999) Am J Pathol 155, 1281-1291.
Smalley, W. E. et al. (1997) Adv Pharmacol 39, 1-20.
Smolarek et al. (2012) Cancer Prey Res (Phila). Nov. 2012;5(11):1310-20.
Sontag, T. J. & Parker, R. S. (2002) JBiol Chem 277, 25290-25296.
Stahl, P., et al., Handbook of Pharmaceutical Salts: Properties, Selection and Use, (VCHA/Wiley-VCH, 2002).
Takahashi, K. et al. (2006) J MolCell Cardiol 41, 544-554.
Terashima et al. Bioorganic & Medicanal Chemistry, 10 (2002) pp. 1619-1625.
Thun, M. J. et al. (1993) Cancer Res 53, 1322-1327.
Van den Berg, W. B. (2001) Arthritis Res 3, 18-26.
Van den Berg, W. B. (2001) Semin Arthritis Rheum 30, 7-16.
Vane, J. R. (1976) Adv Prostaglandin Thromboxane Res 2, 791-801.
Vane, J. R. et al. (1998) Cyclooxygenases 1 and 2. Annu Rev Pharmacol Toxicol 38, 97-120.
Vane, J. R. et al. (1998) Int J Tissue React 20, 3-15.
Williams, J. A. et al. (1997) J Biol Chem 272, 25693-25699.
Wynne, H. A. et al. (1993) Pharmacoeconomics 3, 107-123.
Yokomizo, T. et al. (2001) Arch Biochem Biophys 385, 231-241.
Yoshida, E. et al. (2006) J Invest Demiatol 126, 1533-1640.
Yoshimura, R. et al. (2000) Cancer 89, 589-596.
You, C. S. et al. (2005) JNutr 135, 227-.232.

\* cited by examiner

LONG-CHAIN CARBOXYCHROMANOLS AND ANALOGS FOR USE AS ANTI-INFLAMMATORY AGENTS

CROSS REFERENCE TO RELATED APPLICATIONS

This application is a continuation-in-part of U.S. patent application Ser. No. 13/119,737, filed Mar. 18, 2011, which is a U.S. national application under 35 U.S.C. §371(b) of International Patent Application No. PCT/US2009/057293, filed Sep. 17, 2009, which claims the benefit under 35 U.S.C. §119(e) of U.S. Provisional Application No. 61/098,357, filed Sep. 19, 2008, the entirety of the disclosures of which are incorporated herein by reference.

GOVERNMENT RIGHTS STATEMENT

This invention was made with government support under R01 AT001821, R21 CA152588, & R01 AT006882 awarded by the National Institutes of Health. The government has certain rights in the invention.

BACKGROUND

The immune system plays a central role in maintaining health and disease development. Excessive immune response leads to inflammation, which is characterized by the over-production of pro-inflammatory mediators, including lipid mediators, notably prostaglandins and leukotrienes, and cytokines like TNF-alpha, which in turn aggravate inflammation and lead to excessive damage to host tissues. During inflammation, several lipid mediators, such as prostaglandins and leukotrienes, are synthesized from the essential fatty acid, arachidonic acid (AA), and play important roles in mediating inflammatory response. For instance, prostaglandin $E_2$ ($PGE_2$), which is synthesized from cyclooxygenase (COX)-catalyzed oxidation of AA, is believed to cause pain and fever as well as activate cytokine formation (44). Leukotriene B4, another oxidized product derived from AA through the 5-lipoxygenase (5-LO) catalyzed pathway in neutrophils, is a potent chemotactic agent. Important enzymes for prostaglandin formation are cyclooxygenases, which comprise a constitutive form, COX-1, and an inducible form, COX-2. COX-1 catalyzed TxA2 formation in platelets activates platelet aggregation. The protective effect of low-dose aspirin in cardiovascular disease has been attributed to its inhibition of COX-1-mediated TxA2 generation in platelets. COX-2 is normally expressed in limited tissues but is induced by endotoxin and cytokines in many immune cells including macrophages, monocytes and epithelial cells (45). Under most inflammatory conditions, COX-2 is up-regulated and is the primary enzyme responsible for the formation of pro-inflammatory $PGE_2$. 5-LOX has also been shown to play an important role in inflammatory conditions including experimental colitis.

In addition to the lipid mediators, cytokines also play important roles in regulating inflammatory response. The major pro-inflammatory cytokines, TNF-alpha and Interleukin 1-beta (IL-1beta), are known to activate many immune cells such as monocytes and macrophages. Antibodies against TNF-alpha and IL-1beta are clinically useful in the therapy of certain inflammatory diseases (49, 50).

These pro-inflammatory mediators are also believed to be important in the development of degenerative diseases. For instance, various animal and human tumor tissues have been reported to express the enhanced COX-2 and 5-LOX, as well as their products, $PGE_2$ and 5-HETE. $PGE_2$ has been shown to promote proliferation of certain cancer cells, and NSAIDs can inhibit the growth of carcinoma cells and suppress angiogenesis. In addition to cancer, COX-2 and 5-LOX mediated reactions appear to play a role in cardiovascular diseases. Because of the central roles of $PGE_2$ and $LTB_4$ in inflammation, COXs and 5-LOX have been recognized as targets for drug therapy in inflammatory diseases.

Although drugs targeting COXs have been extensively developed and used in the treatment of inflammatory diseases, they are limited by adverse effects Inhibition of both COX-1 and COX-2 by NSAIDs and selective COX-2 inhibitors reduces the levels of prostaglandins, which leads to a reduction of pain and inflammation. However, a selective shutdown of COXs pathway can cause alternative metabolism of arachidonic acid via the 5-LOX pathway, which results in an increased production of leukotrienes, such as LTB4 and cysteinyl leukotrienes. These leukotrienes are pro-inflammatory and also known to promote gastrotoxicity. Because of the disadvantage of the selective inhibition of specific COXs pathways, a drug targeting COXs and 5-LOX, which can reduce both prostaglandins and leukotrienes, would provide a superior outcome Inhibition of these multiple pathways can not only result in a more potent anti-inflammatory effect, but also reduce potential adverse effect caused by a shunt in arachidonate metabolism to either pathway.

SUMMARY

The following presents a simplified summary of one or more embodiments of the invention in order to provide a basic understanding of such embodiments. This summary is not an extensive overview of all contemplated embodiments, and is intended to neither identify key or critical elements of all embodiments, nor delineate the scope of any or all embodiments. Its sole purpose is to present some concepts of one or more embodiments in a simplified form as a prelude to the more detailed description that is presented later.

Inflammatory diseases affect millions of people in the world and chronic inflammation contributes to the development of degenerative diseases such as cancers, cardiovascular diseases, and neurodegenerative disorders (1-3). Cyclooxygenases (COX) catalyze enzymatic oxidation of arachidonic acid (AA) to prostaglandin H2 (PGH2), the common precursor to prostaglandins and thromboxane, which are important lipid mediators for regulation of inflammatory response and other physiological as well as pathophysiological processes (4, 5). Two COX isoforms have been identified. COX-1 is a constitutive form that regulates homeostasis in mainly tissues, and COX-2 is an inducible form that is mainly responsible for the generation of pro-inflammatory eicosanoids, including prostaglandin $E_2$ ($PGE_2$) under acute inflammatory conditions (5). COX inhibitors, which belong to non-steroidal anti-inflammatory drugs (NSAIDs), have been used for the relief of fever, pain and inflammation (7, 8), as well as treatment for chronic diseases. This disclosure provides conjugated long-chain carboxychromanol compounds useful for treating conditions associated with the need to inhibit cyclooxygenase-1, cyclooxygenase-2, and/or 5-lipoxygenase, such as disorders associated with inflammation of the gut or various types of cancer, and pharmaceutical formulations containing the compounds.

Other aspects and features, as recited by the claims, will become apparent to those skilled in the art upon review of the following non-limited detailed description of the invention in conjunction with the accompanying figures.

BRIEF DESCRIPTION OF THE DRAWINGS

Having thus described embodiments in general terms, reference will now be made to the accompanying drawings, which are not necessarily draw to scale.

Figure 1A:
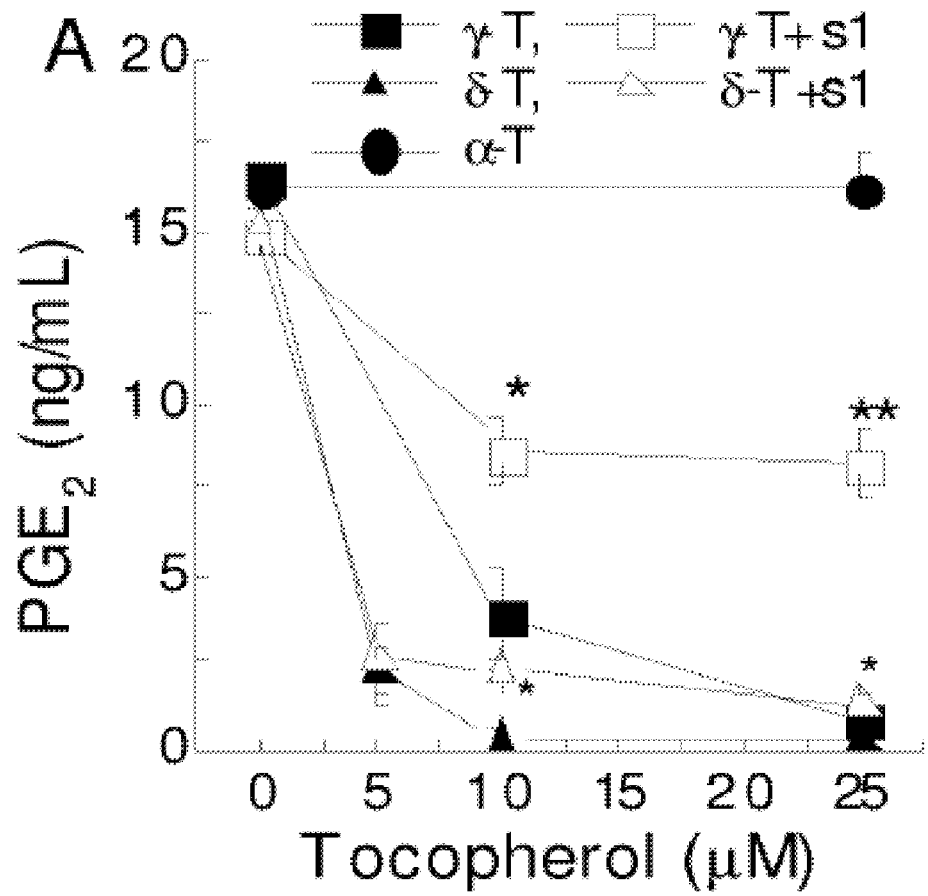

FIG. 1A illustrates that vitamin E forms differentially inhibited PGE2 in IL-1β treated A549 cells and the presence of sesamin partially decreased the inhibitory potency. A549 cells were pre-incubated with different concentrations of tocopherols in the presence or absence of 1 μM sesamin for 15 h, and then treated with IL-1β (2 ng/mL) for 24 h. $PGE_2$ in the cell-culture media was measured by ELISA assays. Results are the averages of three independent experiments and expressed as Mean±SEM.

Figure 1B:
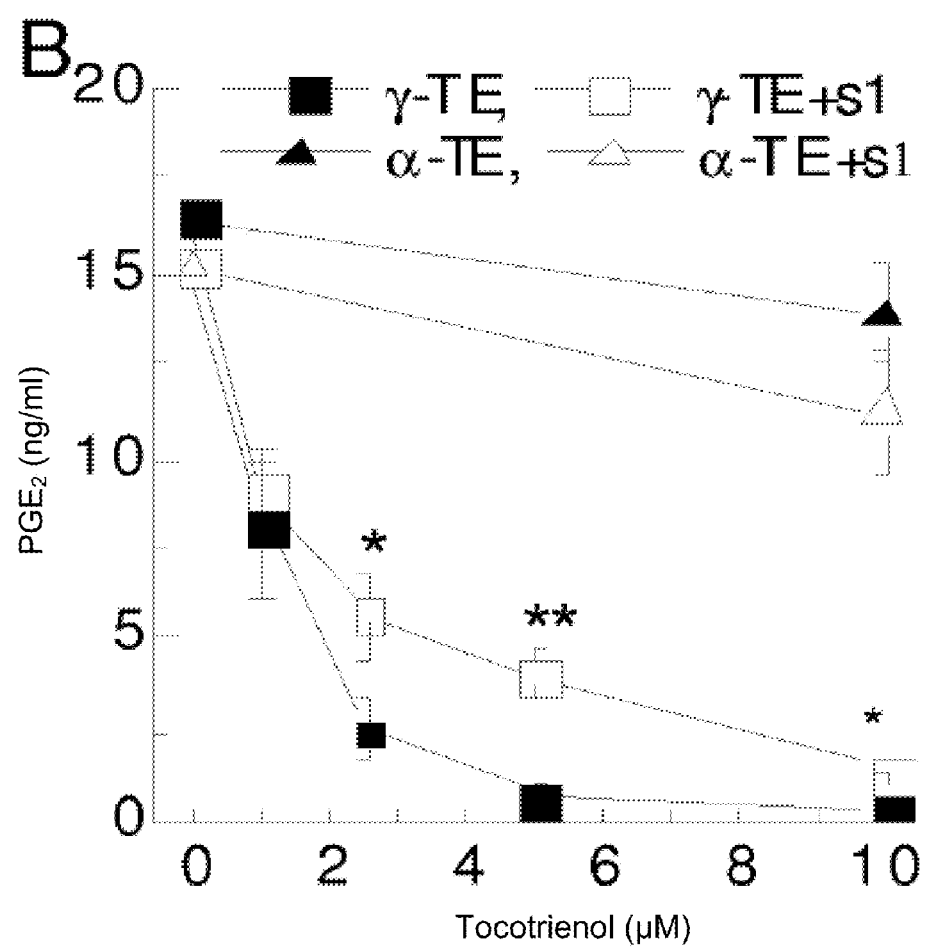

FIG. 1B illustrates that vitamin E forms differentially inhibited PGE2 in IL-1β treated A549 cells and the presence of sesamin partially decreased the inhibitory potency. A549 cells were pre-incubated with different concentrations of tocotrienols in the presence or absence of 1 μM sesamin for 15 h, and then treated with IL-1β (2 ng/mL) for 24 h. $PGE_2$ in the cell-culture media was measured by ELISA assays. Results are the averages of three independent experiments and expressed as Mean±SEM.

Figure 1C:
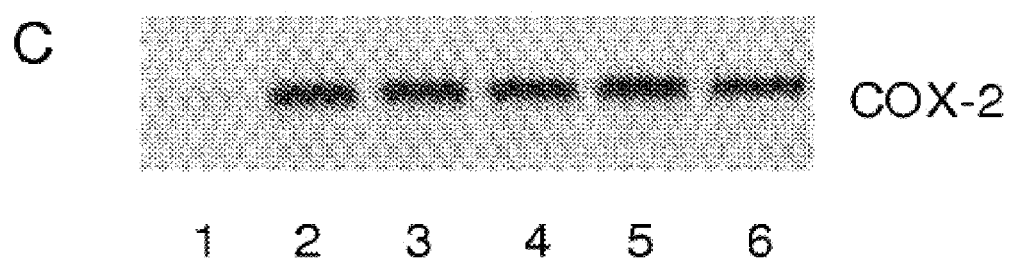

FIG. 1C illustrates that vitamin E forms did not significantly affect COX-2 induction in 1L-1β activated A549 cells. The Western blot showed the effect of vitamin E forms on COX.-2 induction. Cells are treated with vehicle (lane 1); 1L-1β (2 ng/ml, lane 2); or 1L-1β and γ-T at 40 μM (lane 3), or δ-T at 40 μM (lane 4), or α-TE at 10 μM (lane 5), or γ-TE at 10 μM (line 6) for 24-h.

Figure 2A:
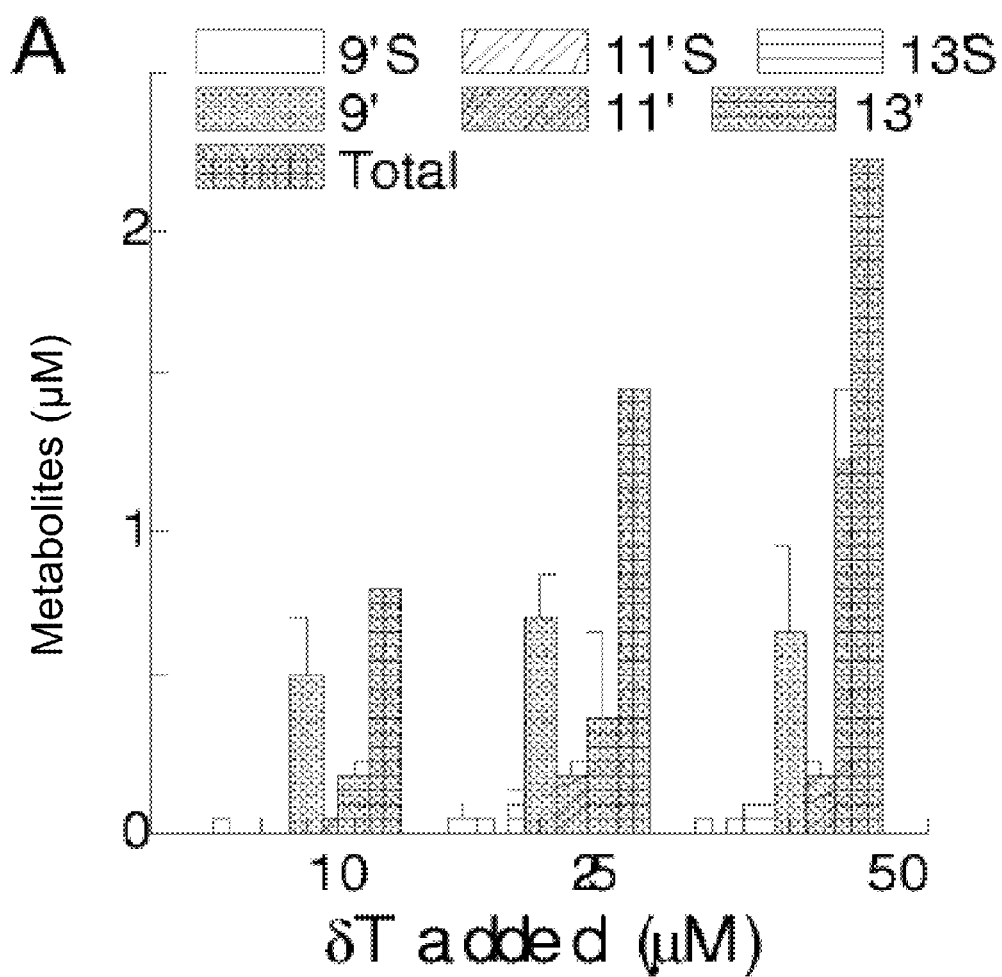

FIG. 2A illustrates dose-dependent accumulation of metabolites of δ-T in cultured media. A549 cells were incubated with δ-T at 10, 25 and 50 μM for 48 h. Media were collected and the metabolites were extracted and measured by HPLC.

Figure 2B:
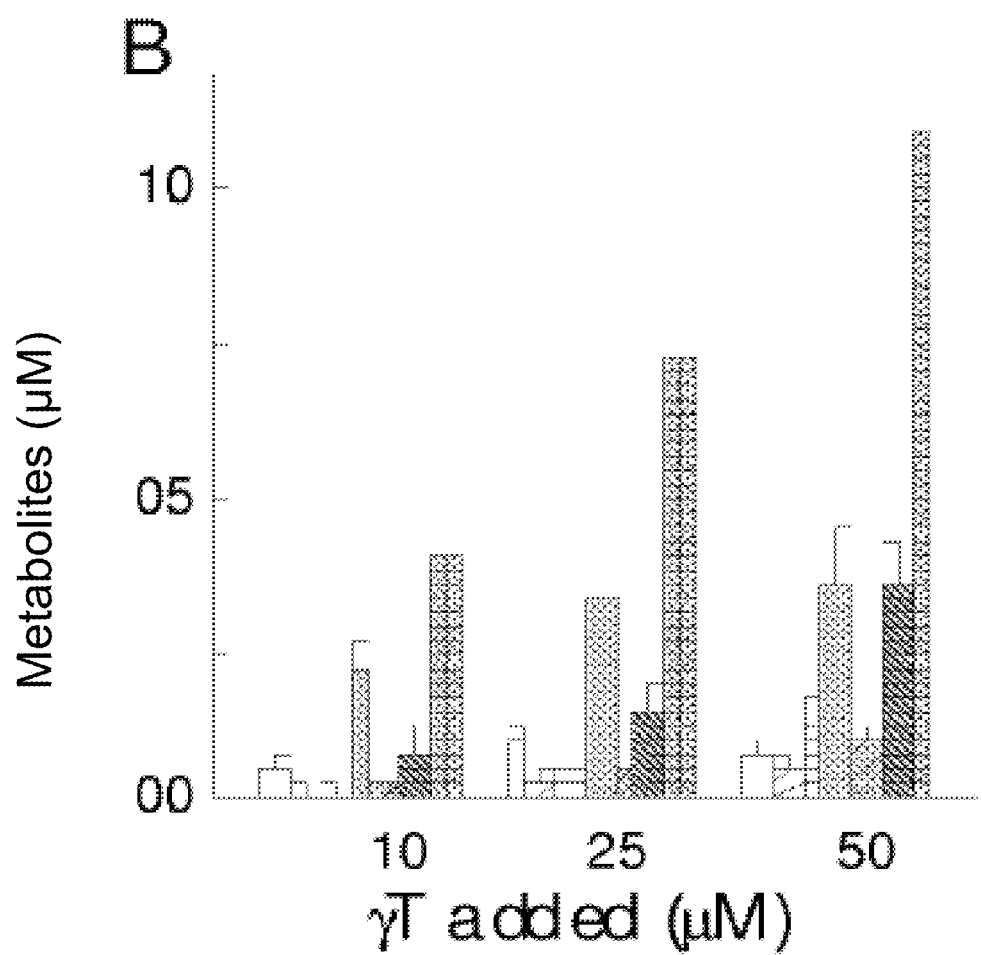

FIG. 2B illustrates dose-dependent accumulation of metabolites of γ-T in cultured media. A549 cells were incubated with γ-T at 10, 25 and 50 μM for 48 h. Media were collected and the metabolites were extracted and measured by HPLC.

Figure 2C:
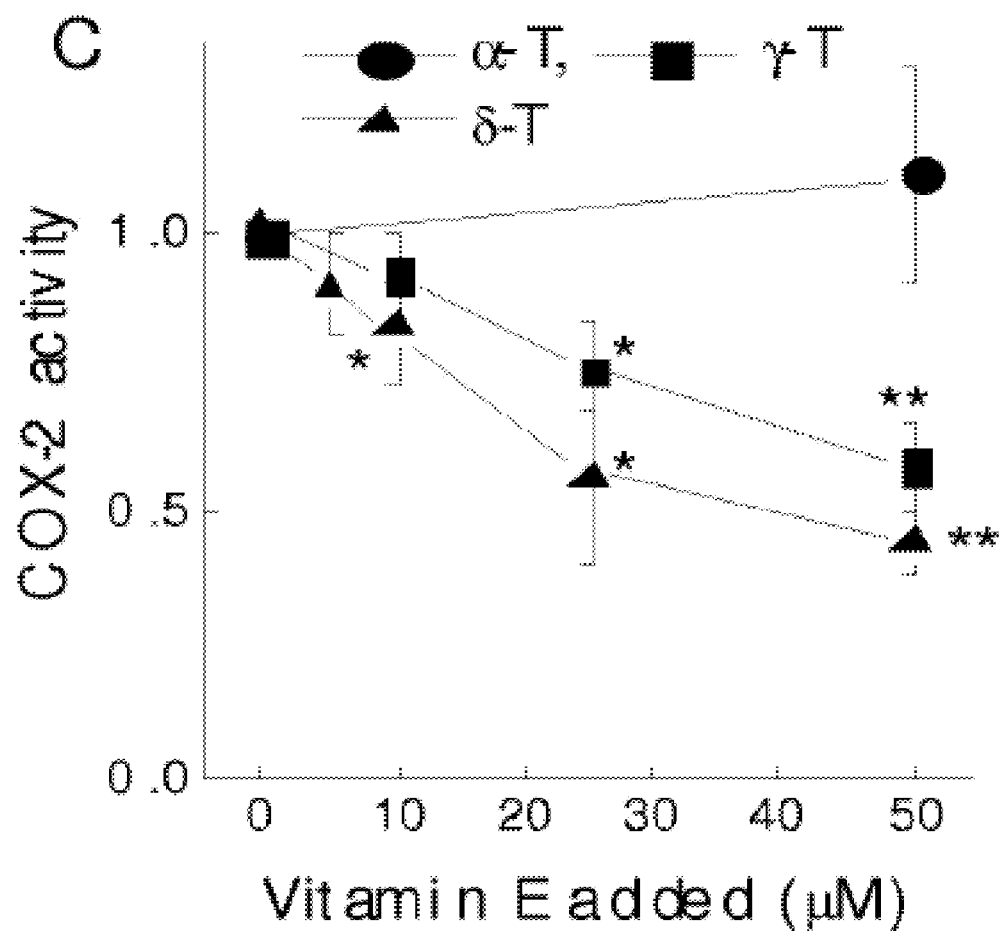

FIG. 2C illustrates that conditioned media showed dose-dependent inhibition of COX activity as assayed in intact cells. A549 cells were activated by 1L-1β (0.1 ng/mL) for 6 h to induce COX-2. Cells with pre-induced COX-2 were then incubated with "metabolites-containing medium" obtained from the experiments disclosed in FIGS. 2A and 2B for 30 min, and then added with AA (5 μM) and incubated for 5 min. Media were collected to measure $PGE_2$ formation. The relative COX activity was expressed as the ratio of $PGE_2$ under each treatment to that of vehicle control media which were obtained under the same condition as metabolite-conditioned media. All the results are averages of three or more independent experiments (Mean±SD).

Figure 3A:
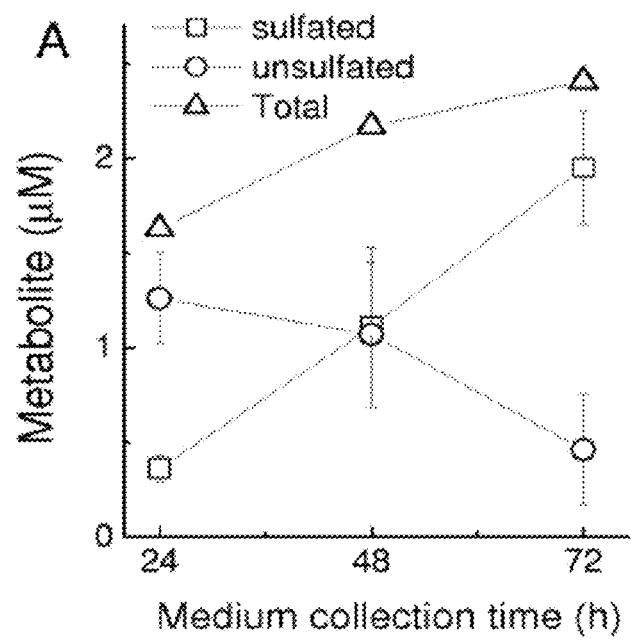

FIG. 3A illustrates that unconjugated long-chain carboxychromanols but not sulfated derivatives inhibited COX-2 activity in intact cells. FIG. 3A showed time-dependent changes of carboxychromanols and sulfated carboxychromanols in A549 cells. Sulfated metabolites were the sum of 9'S, 11'S and 13'S, and unconjugated metabolites are the sum of 9', 11' and 13'. Conditioned media were obtained by incubation of A549 cells with γ-TE at 20 μM for 24, 48 and 72 h. Metabolites were extracted and measured using HPLC assay. The conditioned media were then used for the activity assay as described in FIGS. 2A and 2B. Unsulfated/sulfated is the ratio of the sum of 9', 11' and 13' to that of 9'S, 11'S and 13'S. All the results are expressed as Mean±SD.

Figure 3B:
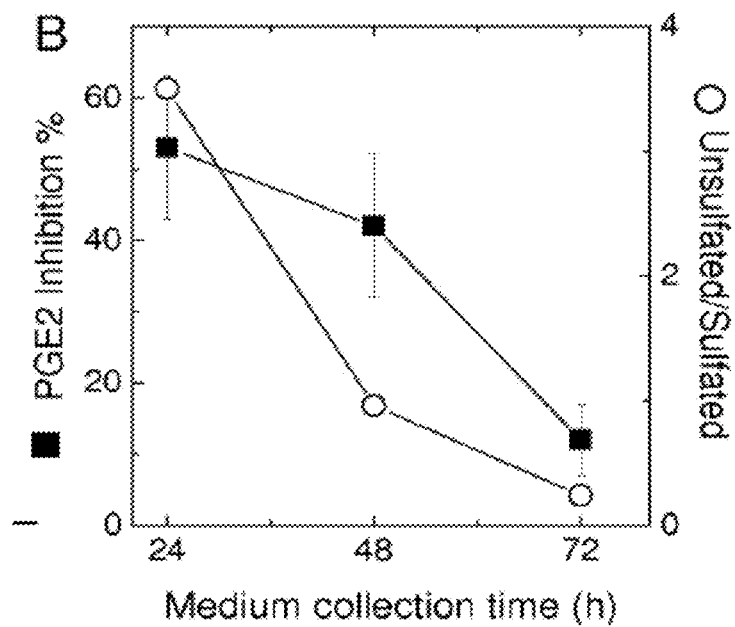

FIG. 3B illustrates the inhibitory potency correlated with the accumulation of unconjugated long-chain carboxychromanols but not that of sulfated forms. Conditioned media were obtained by incubation of A549 cells with γ-TE at 20 μM for 24, 48 and 72 h. Metabolites were extracted and measured using HPLC assay. The conditioned media were then used for the activity assay as described in FIGS. 2A and 2B. Unsulfated/sulfated is the ratio of the sum of 9', 11' and 13' to that of 9'S, 11'S and 13'S. All the results are expressed as Mean±SD.

Figure 4:
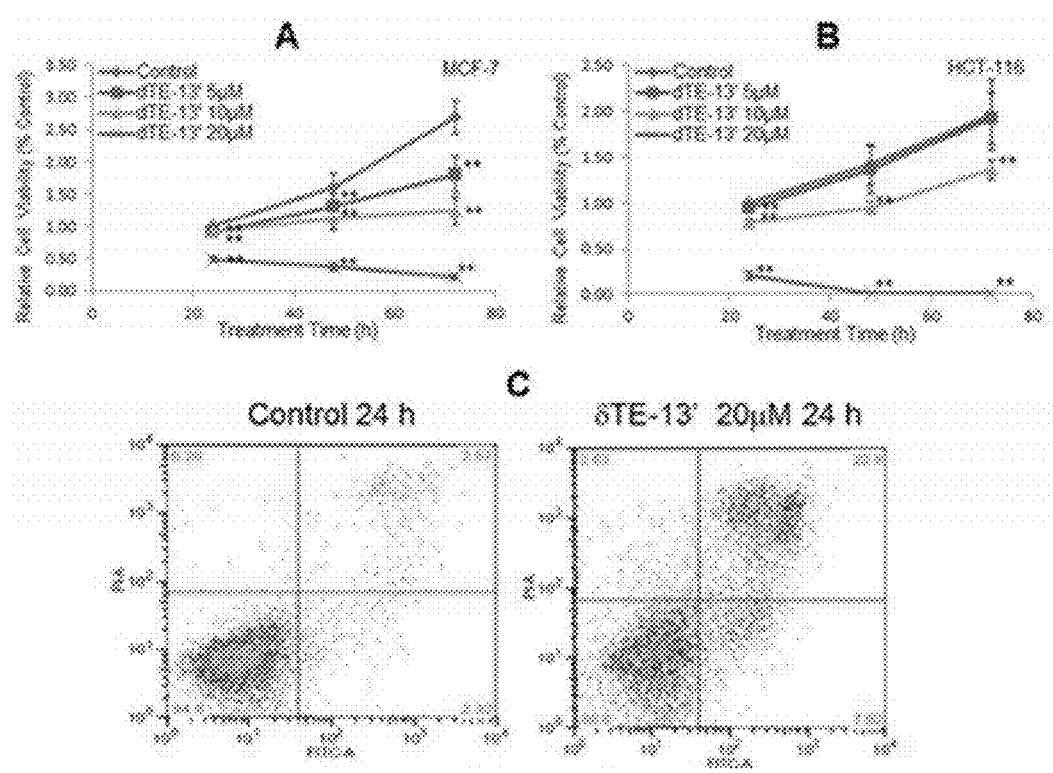

FIG. 4. δTE-13' inhibits cancer cell growth and induces cancer cell death. Panel A shows dose-dependent inhibition of human breast MCF-7 cell growth based on different concentrations of δTE-13' compared to a control, as indicated by MTT assays. Panel B shows dose-dependent inhibition of colon HCT116 cancer cell growth based on different concentrations of δTE-13' compared to a control, as indicated by MTT assays. Panel C shows that δTE-13' effectively kills cancer cells by induction of apoptosis in HCT116 colon cancer cells as indicated by flow cytometry data.

Figure 5:
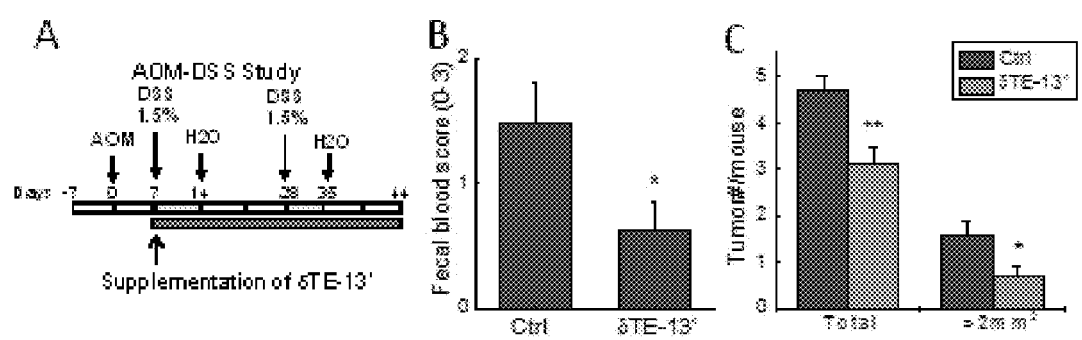

FIG. 5. Effects of δTE-13' on AOM-DSS-induced colon inflammation and tumorigenesis. Panel A shows the study design having δTE-13' at 0.025% (w/w) in AIN93G based diet. Panel B shows a fecal bleeding score on the 7th day of the 2nd cycle of DSS. Panel C shows the effects of δTE-13' on tumor multiplicity. **P<0.01, *P<0.05: significant difference between δTE-13' and control group (n=15-16).

Figure 6:
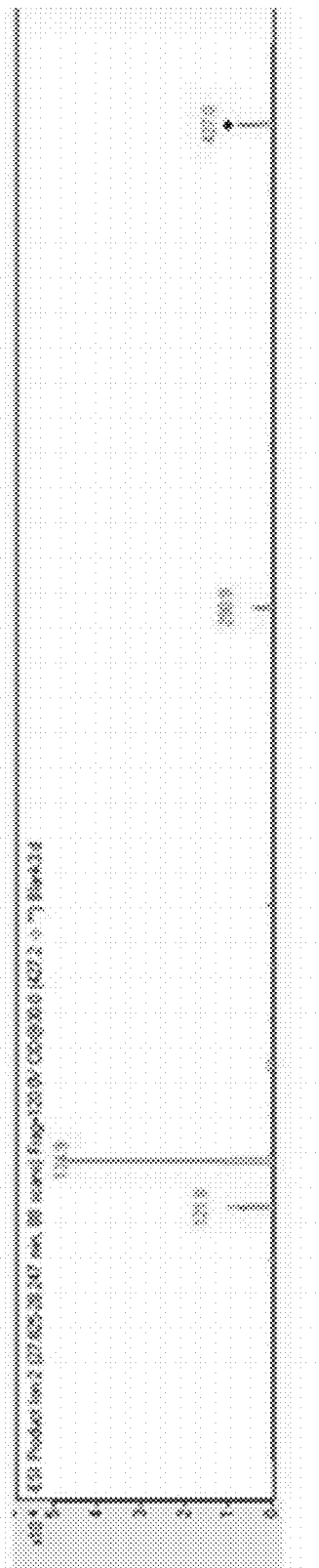

FIG. 6. Detection of δTE-13'-1 in fecal samples. The panel shows a liquid chromatography-mass spectrometry analysis of fecal samples of mice fed with δTE-13'.

Figure 7:
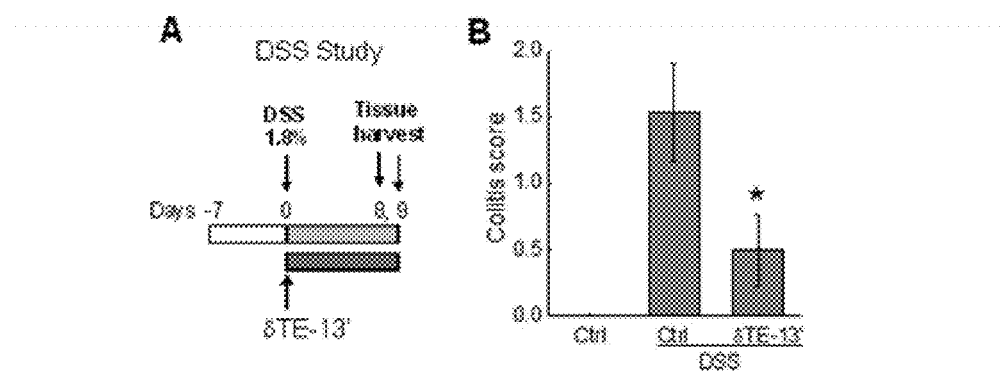

FIG. 7. δTE-13' ameliorated colitis induced by DSS in mice. Panel A shows the study design including when DSS and δTE-13' were introduced and when tissue was harvested. Panel B shows the significant different in DSS-induced diarrhea and fecal bleeding in control mice compared to treatment mice.

DETAILED DESCRIPTION

Embodiments of the present disclosure will now be described more fully hereinafter with reference to the accompanying drawings, in which some, but not all, embodiments are shown. Indeed, the disclosure may be embodied in many different forms and should not be construed as limited to the embodiments set forth herein; rather, these embodiments are provided so that this disclosure will satisfy applicable legal requirements. Additionally, while embodiments are disclosed as "comprising" elements, it should be understood that the embodiments may also "consist of" elements or "consist essentially of" elements. Where possible, any terms expressed in the singular form herein are meant to also include the plural form and vice versa unless explicitly stated otherwise. Also, as used herein, the term "a" and/or "an" shall mean "one or more," even though the phrase "one or more" is also used herein. Like numbers refer to like elements throughout.

Throughout this disclosure, various information sources are referred to and/or are specifically incorporated. The information sources include scientific journal articles, patent documents, textbooks, and websites. While the reference to these information sources clearly indicates that they can be used by one of skill in the art, each and every one of the information sources cited herein are specifically incorporated in their entirety, whether or not a specific mention of "incorporation by reference" is noted. The contents and teachings of each and every one of the information sources can be relied on and used to make and use embodiments of the disclosure.

The disclosure provides long-chain carboxychromanol compounds useful for treating conditions associated with the need to inhibit cyclooxygenase-1, cyclooxygenase-2, and/or 5-lipoxygenase, and pharmaceutical formulations containing the compounds.

DEFINITIONS

The term "carrier" is used herein to describe any ingredient other than the active components in a formulation. The choice of carrier will to a large extent depend on factors such as the particular mode of administration, the effect of the carrier on solubility and stability, and the nature of the dosage form.

The term "patient" refers to mammals, including humans, companion animals, and livestock animals.

"Pharmaceutically acceptable" as used in this application, for example with reference to salts, polyphenolic sulfation inhibitors, and formulation components such as carriers, means substantially non-deleterious to the recipient patient, and includes "veterinarily acceptable," and thus includes both human and animal applications independently.

The term "polyphenolic sulfation inhibitor" includes those compounds which can inhibit the long-chain carboxychromanol compounds from metabolizing or converting in whole or in part to a sulfated form of the compound. Such pharmaceutically acceptable polyphenolic sulfation inhibitors include, for example, sesamin and curcumin.

The term "therapeutic amount" means an amount of a compound sufficient to treat one or more physiological disorders associated an excess of COX-1, COX-2, and/or 5-LOX. The specific dose administered is determined by the particular circumstances surrounding each patient's situation. These circumstances include the route of administration, the prior medical history of the patient, the particular physiological disorder or symptom being treated, the severity of the particular physiological disorder or symptom being treated, and the age and sex of the patient. However, it will be understood that the therapeutic dosage administered will be determined by a physician in light of the relevant circumstances, or by a veterinarian for non-human patents. Generally, a dosage amount of between about 0.01 to 1000 mg/kg of weight of the patient can be employed, and administered once or more daily, weekly, or monthly, depending on the circumstances described above.

The terms "treat", "treating", and "treatment" include ameliorating, halting, slowing, restraining, and reversing the progression of or reducing the severity of the physiological disorders, or their symptoms, associated with the need to inhibit COX-1, COX-2, and/or 5-LOX.

Long-Chain Carboxychromanol Compounds and Method of Using Same

The long-chain carboxychromanol compounds inhibited COX-1, COX-2, and 5-LOX. As such the compounds are of value in the treatment of a wide variety of clinical conditions which are characterized by the presence of an excess of COX-1, COX-2, and/or 5-LOX. Thus, the invention provides methods for the treatment or prevention of a physiological disorder associated with an excess of COX-1, COX-2, and/or 5-LOX, which method comprises administering to a mammal in need of said treatment an effective amount of a long-chain carboxychromanol compound or a pharmaceutically acceptable salt thereof. The terms "physiological disorder associated with an excess of COX-1", or " . . . COX-2", or " . . . 5-LOX" encompass those disorders associated where inhibition of COX-1, COX-2, and/or 5-LOX is desired to alleviate the disorder and/or its symptoms. Such disorders include, for example, arthritis, rheumatoid arthritis, spondyloarthopathies, gouty arthritis, osteoarthritis, systemic lupus erythematosus, juvenile arthritis, gastrointestinal conditions (e.g., inflammatory bowel disease, Crohn's disease, gastritis, irritable bowel syndrome, ulcerative colitis, and the like), colorectal and other cancers, asthma, bronchitis, menstrual cramps, tendinitis, bursitis, skin related conditions (such as, for example, psoriasis, eczema, burns, dermatitis, and the like), vascular diseases, periarteritis nodosa, thyroidiris, aplastic anemia, Hodgkin's disease, scleredoma, rheumatic fever, type I diabetes, myasthenia gravis, sarcoidosis, nephrotic syndrome, Behcet's syndrome, potymyositis, gingivitis, hypersensitivity, conjunctivitis, swelling occurring after injury, myocardial ischemia, and the like, as well as others mentioned elsewhere herein.

Pharmaceutically acceptable salts and common methodology for preparing them are known in the art. See, e.g., P. Stahl, et al., Handbook of Pharmaceutical Salts: Properties, Selection And Use, (VCHA/Wiley-VCH, 2002); S. M. Berge, et al., "Pharmaceutical Salts," Journal of Pharmaceutical Sciences, Vol. 66, No. 1, January 1977. Examples of salts include, but are not limited to, salts formed by standard reactions with both organic and inorganic acids, such as sulfuric, hydrochloric, phosphoric, acetic, succinic, citric, lactic, maleic, fumaric, cholic, pamoic, mucic, glutamic, camphoric, glutaric, glycolic, phthalic, tartaric, formic, lauric, stearic, salicylic, methanesulfonic, benzenesulfonic, sorbic, picric, benzoic, cinnamic and like acids.

The compounds of the present invention are preferably formulated as pharmaceutical compositions administered by a variety of routes including the oral, rectal, transdermal, subcutaneous, topical, intravenous, intramuscular or intranasal routes. Such pharmaceutical compositions and processes for preparing same are well known in the art. See, e.g., Remington: *The Science and practice of pharmacy* (A. Gennaro, et al., eds., 19th ed., Mack Publishing Co, 1995).

In one embodiment, long-chain carboxychromanols and related compounds useful in the invention are of the following formula:

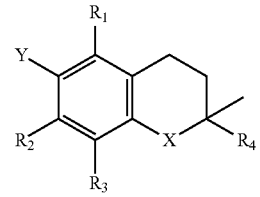

where X is O, $CH_2$, or NH;
Y is OH, NH, —O($C_1$-$C_6$ alkyl), or —OC(O)O($C_1$-$C_6$ alkyl);
$R_1$ is H or $C_1$-$C_6$ alkyl;
$R_2$ is H or $C_1$-$C_6$ alkyl;
$R_3$ is H or $C_1$-$C_6$ alkyl;
$R_4$ is $C_9$-$C_{17}$ straight chain alkyl, optionally substituted by one or more $C_1$-$C_6$ alkyl, and having a carboxy group (—COOH) at its terminal end; and pharmaceutically acceptable salts thereof "$C_1$-$C_6$ alkyl" includes those branched or straight chain substituents having 1 to 6 carbons and includes methyl, ethyl, propyl, butyl, pentyl, hexyl, isopropyl, isobutyl, sec-butyl, tert-butyl, isopentyl, neopentyl, tert-pentyl, isohexyl, and the like. "$C_9$-$C_{17}$ straight chain alkyl" includes those straight chain substituent's having from 9 to 17 in the chain such as nonyl, decyl, undecyl, dodecyl, tridecyl, tetradecyl, pentadecyl, hexadecyl, and heptadecyl, and which may be further substituted with one or more of $C_1$-$C_6$ alkyl. Scheme 1 further illustrates the compounds useful in the invention.

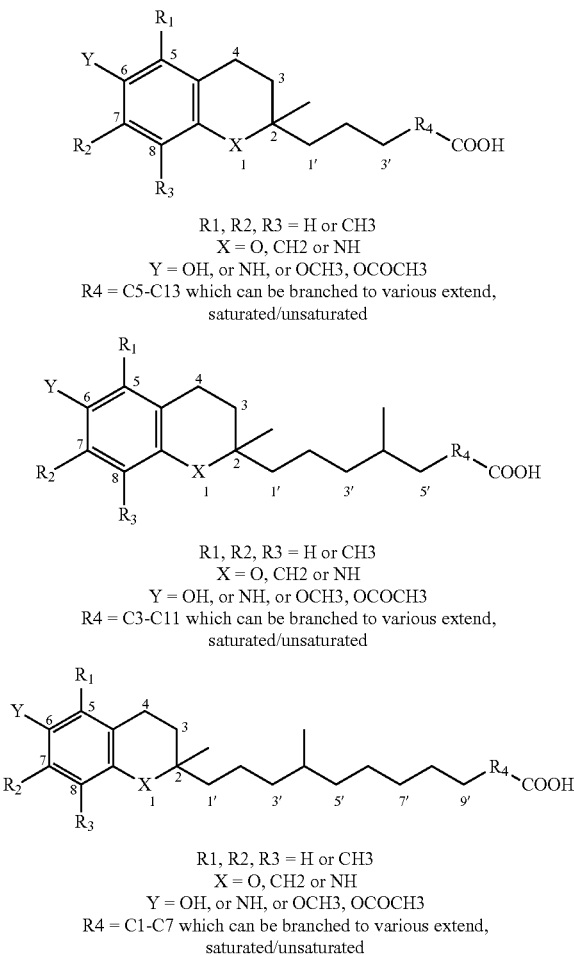

Inflammatory diseases affect millions of people in the world and chronic inflammation contributes to the development of degenerative diseases such as cancers, cardiovascular diseases, and neurodegenerative disorders (1-3). Cyclooxygenases (COX) catalyze enzymatic oxidation of arachidonic acid (AA) to prostaglandin H2 (PGH2), the common precursor to prostaglandins and thromboxane, which are important lipid mediators for regulation of inflammatory response and other physiological as well as patho-physiological processes (4, 5). Two COX isoforms have been identified. COX-1 is a constitutive form that regulates homeostasis in mainly tissues, and COX-2 is an inducible form that is mainly responsible for the generation of pro-inflammatory eicosanoids, including prostaglandin E2 ($PGE_2$) under acute inflammatory conditions (5). COX inhibitors, which belong to non-steroidal anti-inflammatory drugs (NSAIDs), have been used for the relief of fever, pain and inflammation (7, 8), as well as treatment for chronic diseases. It is now well established that NSAIDs are effective and useful chemoprevention agents for colon cancer (9) and possibly other types of cancer (10).

Vitamin E comprises four tocopherols ($\alpha$-, $\beta$-, $\gamma$-, and $\delta$-T) and four tocotrienols ($\alpha$-, ($\beta$-, $\gamma$-, and $\delta$-TE)(Scheme 2). $\alpha$-T is the predominant vitamin E form in the plasma and tissues, as well as in most supplements. $\gamma$-T, primarily found in plant seeds and plant oils, is the major vitamin E form in the US diets (11). $\gamma$-T and $\delta$-T together constitute 70-80% of vitamin E in the US diet. Rich sources of tocotrienols include palm oil, cereal and barley (11). Until recently, $\alpha$-T was the only vitamin E form had drawn most attention and extensively studied. Recent studies by us and others indicate that other forms of vitamin E have distinct bioactivities from $\alpha$-T, and these properties may be important to disease prevention and/or therapy (12). Specifically, we have showed that $\gamma$-T and its terminal metabolite, $\gamma$-CEHC ([(2-carboxyethyl)-hydroxychroman]), inhibited COX-2 catalyzed $PGE_2$ formation in LPS activated macrophage and $1L$-$1\beta$-treated epithelial cells (13). In contrast, $\alpha$-T was much less effective. In a rat inflammation model, we showed that $\gamma$-T and $\gamma$-CEHC inhibited proinflammatory eicosanoid formation and attenuated inflammation-induced damage (14). We also documented that $\gamma$-T, in contrast to $\alpha$-T, inhibited growth and induced death in cancer cells but had no effect on normal epithelial cells (15).

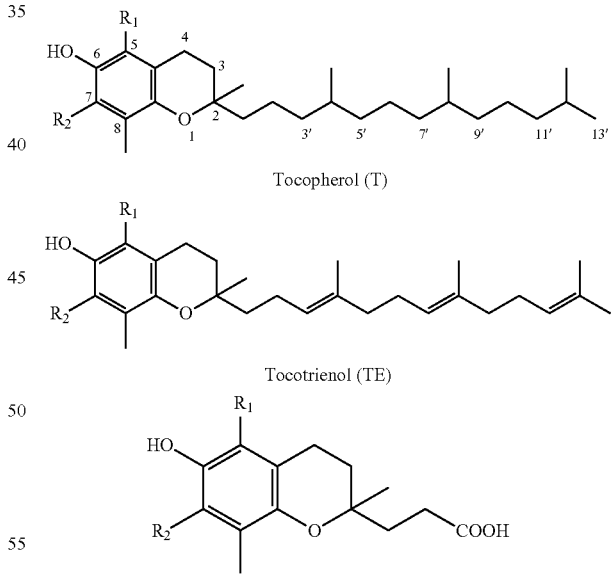

Recently, we and others have shown that vitamin E forms are metabolized to long-chain carboxychromanols, i.e. 9'-, 11'-, 13'-carboxychromanol (16-18) and their sulfated counterparts (17) (Scheme 3).

Scheme 3

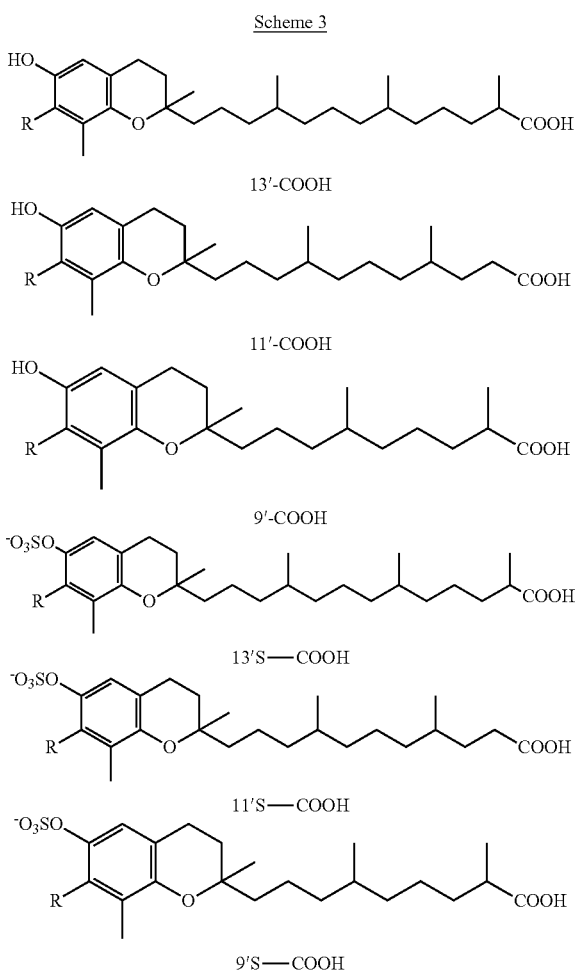

13'-COOH
11'-COOH
9'-COOH
13'S—COOH
11'S—COOH
9'S—COOH

These metabolites are generated by w-hydroxylation and oxidation of the co-terminal carbon to generate 13'-carboxychromanol, followed by a step-wise β-oxidation to remove 2- to 3-carbon moiety each cycle to form shorter side-chain carboxychromanols. The terminal urinary-excreted metabolite is CEHC (3'-carboxychromanol) (16, 19). During this process, significant amounts of sulfated long-chain carboxychromanols are also generated (17). Importantly, we showed that some of these metabolites were found in rat plasma subsequent to supplementation (17).

In the present study, we systemically examined the effect of different vitamin E forms and their metabolites on COX-2 catalyzed $PGE_2$ formation in IL-1β activated human lung A549 cells, as well as the effect on COX activity in enzyme assays. We found that 13'-carboxychromanol is a potent inhibitor of COXs, and carboxychromanols with shorter side chain including 9' and CEHC, as well as vitamin E are weaker inhibitors. On the other hand, the sulfated derivatives appeared to be ineffective.

Materials—

αT (99%), γT (97%, 99%), and δT (97%) were purchased from Sigma (St Louis, Mo.). γ-CEHC (>98%) was from Cayman Chemicals (Ann Arbor, Mich.). α-Tocotrienol (α-TE) and γ-tocotrienol (γ-TE) were a generous gift from BASF (Germany). Tissue culture reagents were from Invitrogen (Rockville, Md.). Monoclonal COX-2 antibody, human recombinant COX-2 and ovine COX-1 were obtained from Cayman Chemicals (Ann Arbor, Mich.). Human recombinant interleukin-1 (IL-1β), sesamin, ketoconazole, dimethyl sulfoxide (DMSO), 3-(4,5-dimethylthiazol-2-yl)-2,5-diphenyl tetrazolium bromide (MTT), and all other chemicals were from Sigma.

Cell Culture—

Human lung A549 cancer cells were obtained from American Type Culture Collection (Manassas, Va.). These cells were routinely cultured in RPMI-1640 with 10% fetal bovine serum (FBS).

$PGE_2$ Generation During Chronic IL-1β Treatment—

$2.5-3 \times 10^5$ A549 cells per well were seeded in RPMI-1640 with 10% of FBS and allowed to attach overnight in a 24-well plate. Vitamin E stock solutions were initially made in DMSO and then diluted in 10 mg/mL of bovine serum albumin. Confluent cells were incubated in DMEM containing 1% FBS with DMSO (control) or vitamin E forms for 14-16 h and then 2 ng/ml of IL-1β was introduced for 24 hours. The medium was then collected and $PGE_2$ accumulation was measured using ELISA assay from Cayman Chemicals (Ann Arbor, Mich.).

COX-2 Activity in Intact Cells—

A549 cells were pre-treated with 0.5-1 ng/mL of IL-1β- for 6 hours to induce COX-2 expression, then incubated with fresh medium containing vitamin E farms, metabolite-containing conditioned medium or control medium for 30 min. In some experiments, isolated 9' and 13', as well as their controls, were added for the 30-min preincubation. The enzyme reaction was initiated by addition of 5 μM AA for 5 min, and medium was collected and immediately frozen to −20 C. $PGE_2$ generated was measured as an index of COX-2 activity using an EIA assay from Cayman Chemicals.

COX-1 and COX-2 Activity Assay Using Purified Enzymes—

The enzymatic reactions were performed in 0.1M Tris (pH 8.0), in the presence of 5 mM EDTA, 2 mM phenol, and 1 μM heme. Tested compounds, including ibuprofen, acetaminophen, isolated 9'-COOH or 13'-COON, were first preincubated with ovine COX-1 or human recombinant COX-2 for 10 min at room temperature. Enzymatic reactions were initiated by addition of AA at a final concentration of 5 μM for 2 min. The reaction was stopped by addition of 0.1 M HCl. Stannous chloride in 0.1 M HCl was then added to reduce $PGG_2$ and $PGH_2$ to $PGF_{2a}$. After addition of 0.5 vol of 03M NaCl, prostaglandins formed in the reaction were extracted using 2.5 vol of ethyl acetate and the organic layer was completely dried under $N_2$. $PGF_{2a}$ and $PGE_2$ were quantified using ELISA assays from Cayman Chemicals. Under these experimental conditions, $PGF_{2a}$ is the predominant product.

Cellular Uptake of Vitamin E Forms—

Cells were incubated in DMEM containing 1 FBS supplemented with different vitamin E forms for 24 hours. After harvested by scraping, cells were washed twice with HBSS. Cellular uptake of vitamin E was then quantified using an HPLC with EC detection (13).

Conditioned Medium Containing Long-Drain Vitamin E Metabolites—

A549 cells were seeded in RPMI-1540 with 10% FBS at a density of $8 \times 10^5$ cells per well in 6-well plates. Twenty-four hours later, media were replaced with fresh DMEM containing 1% FBS with vitamin E forms, or DMSD (0.05%) in controls. Cells were incubated for 24-72 h as specified in the results. Metabolite-containing media were collected, frozen immediately and stored in −20° C. until use.

Quantitation of Vitamin E Metabolites in Conditioned Media—

Long-chain carboxychromanols and their sulfated counterparts were quantitated by a HPLC assay with fluorescent detection (17). Briefly, 8 µL of ascorbic acid (11 mg/mL) was added to 400 µL of conditioned medium, which was then mixed with 10 µL of ethanol and 500 µL of hexane. The mixture was vortexed for 1 min, and followed by centrifugation at 13000 rpm for 2 min. The hexane layer was discarded and the aqueous phase was acidified using 14 µL of acetic acid. The aqueous phase was extracted twice with 1 mL of ethyl acetate, vortexed and centrifuged. The combined ethyl acetate layers were dried under nitrogen. The residue was reconstituted in 200 µl of 70% MeOH/30% water and injected onto the HPLC column.

Extracted metabolites were separated using HPLC and detected by a Shimadzu RF-10AXL spectrofluorometric detector (Shimadzu, Columbia, Md.) with the excitation and emission wavelength at 292 nm and 327 nm, respectively. The mobile phases included A—35% acetonitrile, 65% 10 mM ammonium acetate at pH 4.3 and B—96% acetonitrile, 4% 10 mM ammonium acetate at pH 4.3. The metabolites were separated on a 5 micron Supelcosil LC-18-DB column, 4.6×150 mm (Supelco, Bellefonte, Pa.) using a flow rate of 1.0 mL/min with the following gradient: maintaining 100% A for 8 min, linearly increasing to 100% B from 8 to 30 min, maintaining 100% B until 55 min and then back to 100% A at 56 min. γ-CEHC was quantified using the authentic standard as the external standard. Long-chain metabolites were quantified using tocopherols as the external standards with a correction factor based on the linear relationship between fluorescent intensity and solvent content (17).

Western Blot—

Cells were lysed in Tris-EDTA, 1% SIDS, 1 mM DTT with protease inhibitor cocktails (Sigma) and the resulting solution was heated at 95° C. for 5 min. Equal amounts of protein (10-25n) were loaded on 10-12% pre-cast SDS-PAGE gels (BioRad, Richmont Calif.). Resolved proteins were transferred onto a PVDF membrane (Millipore) and probed by antibodies. Membranes were exposed to chemiluminescent reagent (NEN, Life Science Products) and visualized on a Kodak film using a M35A X-GMAT processor (Kodak).

Statistical Analysis—

The unpaired student's t-test was used in the statistical analysis. All results are expressed as mean±SD. Activation of human lung epithelial A549 cells by IL-1β leads to a strong up-regulation of COX-2 protein expression and almost 100-fold increase of $PGE_2$ generation. This cellular system has been employed to evaluate inhibitory potency of anti-inflammatory drugs, including COX inhibitors and was previously used by us to study the effect of α-T, γ-T and γ-CEHC on $PGE_2$ formation (13, 20). In the present study, we found that various forms of vitamin E differentially inhibited prostaglandin $E_2$ ($PGE_2$) formation when A549 cells were co-treated with IL-1β and vitamin E forms (FIG. 1). Compared with γ-T, δ-T and γ-TE appeared to be even stronger inhibitors, whereas α-T, β-T (no inhibition at 50 µM) and α-TE (20% inhibition at 20 µM) are much less effective at physiologically relevant concentrations Inhibition of $PGE_2$ by γ-T, and γ-TE was also observed in the presence of exogenous AA, where after co-incubated with vitamin E forms and IL-1β, cells were incubated with fresh media containing 5 µM of AA for 5 min. Under this condition, the concentrations of γ-T, δ-T and γ-TE to cause 50% inhibition increased to 25, 10 and 10 µM, respectively. This suggests that the inhibition was independent of substrate availability, and vitamin E forms appear to be stronger inhibitors in the presence of endogenous AA. Using Western Blot, we found that co-incubation with vitamin E forms did not significantly affect the induction of COX-2 protein in response to IL-1β activation (FIG. 1C), which is consistent with our previous observations (13). These results suggest that the inhibitory effect may stem from their inhibition of COX activity.

It has been demonstrated that γ-Y, δ-T, and γ-TE are metabolized in A549 cells to form long-chain carboxychromanols, i.e., 9', 11', and 13' (17, 18) and sulfated carboxychromanols, 9'S, 11'S, and 13'S (17). To investigate whether the metabolism of vitamin E forms affect their inhibition of $PGE_2$, we used sesamin, which is an inhibitor of tocopherol ω-hydroxylase (21) and almost completely inhibited the catabolism of vitamin E forms (17). The presence of sesamin significantly reduced the inhibitory potency of γ-T, while sesamin alone, at 1 µM, did not affect $PGE_2$ generation (FIG. 1A). Sesamin also moderately diminished the inhibitory potency of δ-T and γ-TE (FIGS. 1 A and B). The similar effect was observed with the presence of another cytochrome P-454 inhibitor, ketoconazole. These observations suggest that inhibition of $PGE_2$ is, in part, attributed by the metabolites generated from vitamin E in this cellular system.

We then examined whether vitamin E forms affect cell viability because previous studies showed that γ-T and δ-T inhibited growth and induced apoptosis in several cancer cell lines (15, 22). Under the current experimental conditions, where cells were 100% confluent and incubated with vitamin E in the presence of 1% FBS, γ-T at 25-50 µM, δ-T at 25-50 µM and γ-TE at 20 µM, did not show significant effects on cell viability, as indicated by MTT assays and no apparent changes in cell morphology during the period of entire incubation.

To investigate whether vitamin E metabolites directly inhibit COX activity, we tested a potentially inhibitory effect of conditioned media, which were obtained by incubation of vitamin E forms with A549 cells to generate long-chain carboxychromanols and sulfated carboxychromanols (17). Concentrations of carboxychromanols and sulfated carboxychromanols in conditioned media, as quantified by a sensitive HPLC assay with fluorescent detection (17), appeared to increase proportionally with the dose of added vitamin E forms (FIG. 2A). When tested in intact-cell assays, these metabolite-containing media showed dose-dependent inhibition of COX-2 activity in the presence of endogenous AA (FIG. 2B). Conditioned media from δ-T were slightly more potent than those from γ-T, probably because of higher concentrations of metabolites (FIG. 2). Three control experiments were performed to confirm that the inhibition was due to the metabolites rather than the precursor vitamin or non-specific oxidation products. Specifically, media obtained by a co-incubation of vitamin E and sesamin, or from a cell-free system failed to show any inhibitory effects. In addition, freshly γ-made vitamin E forms did not directly show inhibition under the assay condition (Materials and Methods) (Experimental Conditions in FIG. 2).

Our previous studies showed that the terminal metabolite of γ-T, γ-CEHC, inhibit COX-2 activity using the intact cell assays (13). Because no significant amount of γ-CEHC were found in A549 cells (17), we reasoned that long-chain metabolites are responsible for the reduction of COX-2 activity.

We next asked whether COX inhibition stems from non-conjugated long-chain carboxychromanols, or sulfated derivative, or both. We took advantage of the observation that 90% metabolites from γ-TE were unconjugated carboxychromanols during the first 24-h incubation, whereas more than 85% metabolites were sulfated carboxychromanols when media were obtained after 72-h incubation (FIG. 3A). Using the conditioned media obtained after 24, 48 and 72 h incubation, we found that the inhibitory potency gradually diminished when metabolites shifted from non-conjugated long-chain carboxychromanols (at 24 h) to sulfated derivatives which became predominant at 72 h (FIG. 3B). In contrast, for metabolites from δ-T which had minimal formation of sulfated metabolites (FIG. 2, (17)), a time-dependent enhanced inhibitory potency was observed parallel to a time-dependent increase of non-conjugated metabolites. These findings strongly suggest that carboxychromanols but not their sulfated metabolites are mainly responsible for the observed inhibitory effect.

To directly examine the effect of long-chain metabolites on COX activity, we purified and isolated 9'- and 13'-carboxychromanol (Scheme 4) from δ-T-conditioned media, because of their relative abundance.

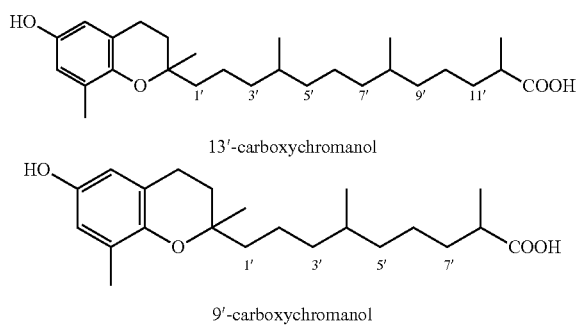

Scheme 4

13'-carboxychromanol

9'-carboxychromanol

In the activity assay in intact cells, we found that both purified metabolites potently inhibited COX-2 activity. On the other hand, the same fraction isolated from control media at the same retention time on HPLC, did not show significant effect. The IC5Os for 9' and 13'-carboxychromanol as assayed in intact cells was approximately 5-10 μM (Table 1). Under the same conditions, ibuprofen and acetaminophen also inhibited COX-2 activity with IC5Os of 5 and 300 μM, respectively.

TABLE 1

Long-chain carboxychromanols are inhibitors of COX-1 and COX-2. The effect of purified carboxychromanols, 9' and 13', on COX activity was assayed in intact cells and using purified enzymes, as described in Materials and Methods. Results were obtained based on two or three independent experiments and expressed as mean + SD.

| IC50 (μM) | COX-2 | COX-1 In A549 cells | COX-2 |
|---|---|---|---|
| 9' | 7 ± 2 | Not inhibit* | Not inhibit* |
| 13' | 6 ± 2 | 5 ± 2 | 4 ± 2 |
| γ-CEHC | 30-70$^a$ | 300 ± 50 | 450 ± 50 |

TABLE 1-continued

Long-chain carboxychromanols are inhibitors of COX-1 and COX-2. The effect of purified carboxychromanols, 9' and 13', on COX activity was assayed in intact cells and using purified enzymes, as described in Materials and Methods. Results were obtained based on two or three independent experiments and expressed as mean + SD.

| IC50 (μM) | COX-2 | COX-1 In A549 cells | COX-2 |
|---|---|---|---|
| Ibuprofen | 5 ± 2 | 8 ± 2 | 5 ± 1 |
| Acetaminophen | 300 ± 50 | Not inhibit* | Not inhibit* |

*9' and acetaminophen at 20 and 250 μM, respectively, did not show any effect of COX-1 or COX-2 activity.
$^a$previously reported (Grammas, 2004 #41; Jiang, 2000 #2).

Potential inhibition of COX-1 or COX-2 was further examined in enzyme-based assays. We found that 13'-carboxychromanols inhibited COX-1 and COX-2 activity with an apparent IC50 of 4-7 μM, which is similar to that of ibuprofen (Table 1). On the other hand, 9'-carboxychromanols at the maximum concentration of 20 μM did not inhibit either enzyme. We were not able to evaluate the inhibitory effect of 9' at higher concentrations because of its limited resources. As a comparison, acetaminophen did not significantly inhibit COX-1 or COX-2 at 250 μM in this assay system (Table 1). F-CEHC showed inhibitory effect at higher IC5Os (300-500 μM). Vitamin E forms are not effective at 50 μM, the highest concentration used.

To further understand the differential effect observed between 9' and 13', we used computer simulation to test the relative binding affinity. The data showed although both 9' and 13' appear to fit in the substrate binding pocket of COX-2, 13' can interact more favorably with the enzyme, compared with 9'. This is consistent with the results from enzyme assays (Table 1).

Cyclooxygenase-catalyzed generation of proinflammatory eicosanoids plays important roles in regulation of inflammatory response and contributes to chronic diseases such as cancer. A major finding of the current study is that long-chain carboxychromanols, which can be generated from vitamin E forms via co- and P-oxidation of the phy-tyl chain in cells and rats (17, 18), are potent inhibitors of cyclooxygenases (Table 1). On the other hand, the sulfated carboxychromanols, which can also be derived from vitamin E (17), appear to be ineffective (FIG. 3). We demonstrated that although both 9' and 13' inhibited COX-2 activity in intact cells, 13' was a much more potent inhibitor of COX-1 and COX-2, as indicated by enzyme-based assays, where 13' shoved inhibitory potency similar to ibuprofen, a commonly used NSAID (Table 1). Compared with long-chain carboxychromanols, γ-CEHC and vitamin E forms, such as γ-T, δ-T and γ-TE but not α-T, β-T or α-TE, appeared to be relatively weaker inhibitors of COX-2. Our study therefore identified certain long-chain carboxychromanols as novel COX inhibitors.

The observation that 13' is a more potent inhibitor than vitamin E forms, 9' and 3' (γ-CEHC) indicates that the conversion of 13'-carbon to a carboxylic acid, and the length of side chain are important factors for COX inhibition by these chromanol analogs. It is known that the carboxylate group of A, forms ion pair or a hydrogen bond with the guanidinium group of a conserved arginine (Arg120), and Tyr355 (23, 24). The importance of these interactions is evident by the observation that site-directed mutagenesis of Arg120 renders the protein resistant to inhibition by carboxylic acid-containing NSAIDs or certain COX-2 inhibitors (25), and increases the Km for AA binding (26,27).

It is conceivable that the carboxylate group in long-chain carboxychromanols is likely to have similar interaction with the guanidinium group of Arg120 and Tyr355, whereas no such interaction can be formed with vitamin E forms. Using computer simulation, we found that both 13' and 9' can form an extended L-shaped conformation to fit in the substrate binding pocket of COX-2, and appeared to be capable of interacting with Arg120 and Tyr355. And yet, 13' appears to interact stronger than 9' with other hydrophobic amino acids at the substrate-binding site of the enzyme. Similarly, the longer side chain of 9' renders it stronger interaction with the enzyme than γ-CEHC. In addition, the current study showed that sulfated long-chain carboxychromanols do not inhibit COX activity (FIG. 3). This may be due to the strong polarity of the sulfate group which cannot interact favorably with the majority of hydrophobic amino acids at the binding site.

In a further embodiment, 13'-carboxychomanol analogs with conjugation at the phenolic group, i.e., δT-13'-R and δTE-13'-R, have been determined to be useful for prevention and treatment of cancer and inflammatory diseases. These conjugated 13'carboxychromanol analogs are shown in scheme 5, which depicts variants of scheme 1 with conjugation at the phenolic group for both tocopherols (A) and tocotrienols (B). Dual inhibition of COX and 5-LOX is an important anti-inflammatory and anticancer property for prevention and treatment of cancer and inflammatory diseases (9, 63-65). Dual inhibition of COX and 5-LOX has advantages over non-steroid anti-inflammatory drugs such as NSAIDS, COX inhibitors, etc., by inhibiting multiple pro-inflammatory pathways with reduced adverse effects (66). Because of this activity, δTE-13' is effective in the treatment and prevention of cancer and inflammatory diseases.

The 13'-carboxychromanol analog may be conjugated to an acetyl group forming an acetate, a methyl group forming a methoxy group, or a hydrogen ion forming a hydroxyl group, or the like. In some embodiments, an advantage of using conjugated compounds (δT-13'-R or δTE-13'-R) instead of unconjugated compounds (δT-13' or δTE-13') is that conjugated compounds are less sensitive to oxidation and have better shelf life but are equally effective against cancer. For example, an acetate conjugate can be hydrolyzed to form unconjugated carboxychromanols in the body to become active. An example of hydrolysis of conjugated compounds has been described with tocopheryl acetate (70, 71).

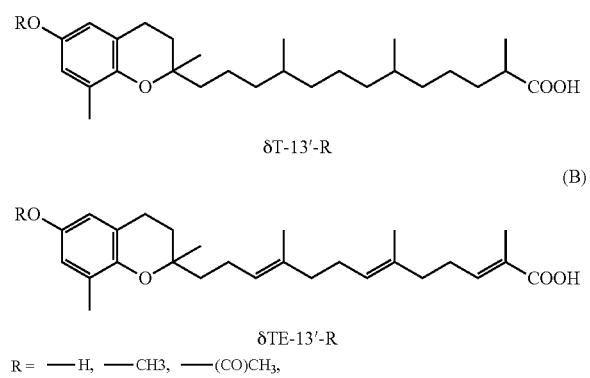

Scheme 5

Specific examples of conjugated 13'-carboxychromanol analogs are shown in Scheme 6 below. For example, 13-(6-hydroxy-2,8-dimethylchroman-2-yl)-2,6,10-trimethyltridecanoic acid is δT-13' analog. Importantly, new research has indicated that δTE-13' analogs such as (2E,6E,10E)-13-(6-hydroxy-2,8-dimethylchroman-2-yl)-2,6,10-trimethyltrideca-2,6,10-trienoic acid are effective in dual inhibition of COX and 5-LOX, in inducing cancer cell death, in suppression of tumorigenesis in a colon cancer model, and in mitigating experimental colitis in mice.

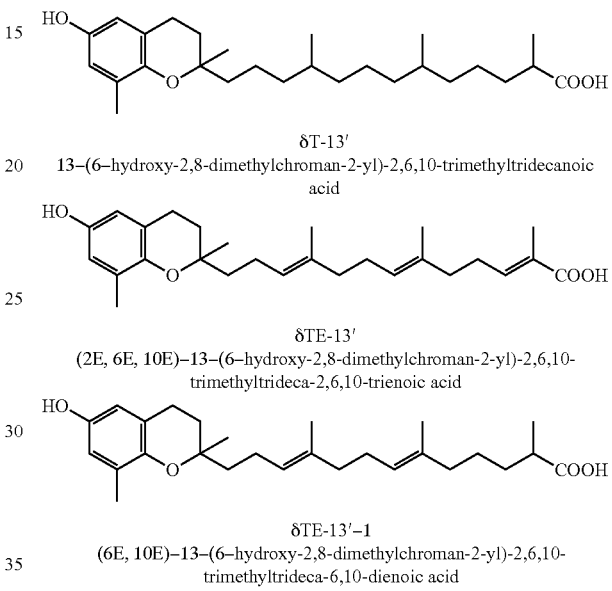

A recent study indicates that δTE-13' as shown in Scheme 6 inhibits both cyclooxygenase (COX) and 5-lipoxygenase (5-LOX), similar to δT-13'. Table 2 discloses the inhibitory effect of 13'-COOHs on COX-2 and 5-LOX. The enzyme assays with purified COX were conducted as described in ref (67). Effects on 5-LOX activity were assessed by the ferrous oxidation-xylenol orange assay (68, 69).

TABLE 2

Inhibitory effect of 13'-COOHs on COX-2 and 5-LOX.

| IC50 (μM) | δT-13' | δTE-13' |
|---|---|---|
| COX-2 activity in intact cells | 4 ± 2 | 4 ± 1 |
| Human recombinant 5-LOX (9U) | 4 ± 1 | 2 ± 0.5 |

As shown in table 2, the COX-2 activity in intact cells was inhibited in a similar manner by both δT-13' and δTE-13'. Unexpectedly, δTE-13' exhibited an even greater effect on inhibition of human recombinant 5-LOX activity compared to δT-13'.

Turning now to FIG. 4, additional research has identified that δTE-13' dose-dependently inhibits human breast MCF-7 cancer call growth (panel A) and colon HCT116 cancer cell growth (panel B), as indicated by MTT assays. As shown in FIG. 4A and FIG. 4B, concentrations of δTE-13' at 5 μM, 10 μM, and 20 μM were compared to a control for over 60 hours. The relative cell viability as a percentage of the control was determined for control and for each concentration. As the concentration of δTE-13' increases, the trend in cell viability changes. For both cell types, when the concentration reaches 20 µM δTE-13' the trend in relative cell viability is negative over time.

In FIG. 4C, flow cytometry data is presented that indicates that δTE-13' effectively kills cancer cells by induction of apoptosis in HCT116 colon cancer cells. In the flow cytometry data, the control indicates that the cancer cells were predominately healthy (lower left quadrant, 94.8%) with only small portions in early stage apoptosis (lower right quadrant, 2.32%) or late stage apoptosis (upper right quadrant, 2.57%). In contrast, cancer cells in the treatment group had a much larger proportion in early stage apoptosis (lower right quadrant, 7.92%) and late stage apoptosis (upper right quadrant, 22.9%) when treated with 20 µM δTE-13' after 24 hours. Similar data were observed with δT-13' (data not shown).

In FIG. 5, the effect of δTE-13' on tumorigenesis in azoxymethane (AOM)/dextran sulfate sodium (DSS)-induced colon cancer in Balb/c mice is investigated. AOM is a carcinogen and DSS administered in drinking water causes colon inflammation that promotes colon tumorigenesis. Therefore, the AOM-DSS model represents inflammation (colitis)-promoted colon cancer. In FIG. 5A, the experimental design is shown. At day 0, AOM is administered to the Balb/c mice. 1.5% DSS in drinking water is introduced and δTE-13' (0.025% w/w) supplementation in AIN93G based diet begins at day 7. Water is introduced at day 14, 1.5% DSS is introduced at day 28, and water is again introduced at day 35. δTE-13' supplementation continues throughout the study. The δTE-13' supplementation at 0.025% diet had no effect on body weight and food intake (data not shown), but significantly attenuated DSS-induced inflammation as indicated by decreased fecal bleeding during the second cycle of DSS. δTE-13' significantly suppressed AOM/DSS-induced tumorigenesis in the colon, as indicated by decreased total tumor multiplicity by 34% ($P<0.01$) and large polyps by 58% ($P<0.05$). These results indicate that δTE-13'-COOH appears to be safe and effective in suppression of colon cancer.

For example, in panel B of FIG. 5, the fecal bleeding score (0-3) is provided for the $7^{th}$ day of the $2^{nd}$ DSS cycle. As shown in the panel, the treatment group has a significantly decreased fecal bleeding score compared to the control ($p<0.05$). Similarly, in panel C of FIG. 5, the total number of tumors and number of large ($>2$ mm$^2$) tumors is significantly decreased in mice receiving the δTE-13' treatment compared to a control. N=15-16.

Turning now to FIG. 6, using liquid chromatography-mass spectrometry, the formation of δTE-13'-1 (Scheme 6, the 3rd structure) in fecal samples of mice fed with δTE-13' was detected. Due to structural similarity with other 13' analogs, such as δTE-13', we concluded that this compound contributes to anti-inflammatory and anticancer effects.

In FIG. 7, data from a DSS-induced colitis model indicates that δTE-13' in diet significantly mitigated DSS-induced diarrhea and fecal bleeding. In panel A, the study design is shown indicating that DSS and δTE-13' are introduced at day 0 and tissue is harvested at day 8 or 9. In panel B, the colitis score is determined for an untreated control (no colitis), a DSS-treated control (high colitis score), and a DSS and δTE-13'-treated mouse (significantly decreased colitis score compared to the DSS-treated control). These results indicate that δTE-13' may be used to treat inflammatory bowel diseases including colitis.

Although carboxychromanols appear to be able to bind to the AA binding site and therefore can presumably inhibit COX activity by competing with the substrate binding, the exact mechanism underlying the inhibition needs to be further elucidated. COXs are bifunctional enzymes that carry out two sequential activities, i.e., the cyclooxygenase activity which leads to the formation of prostaglandin $G_2$ (PGG$_2$) and peroxidase activity which reduces PGG$_2$ to PGH$_2$ (28). Inhibition of peroxidase activity does not require specific binding to the AA site. In theory, chromanol analogs are able to inhibit peroxidase activity, like other phenolic reductants. In fact, O'Leary et al. (29) reported that γ-T and α-T inhibit peroxidase activity of COX-2. However, it is believed that there is no direct correlation between the efficacy as a peroxidase reductant and its potency as an inhibitor of the COX activity (28). Our current and five previous studies (13) indicate that vitamin E forms are weak inhibitors of COXs.

The inhibitory effect of 9', γ-CEHC, and certain forms of vitamin E showed discrepancy between cell-culture and enzyme-based assays. Thus, in IL-1β activated A549 cells, γ-T, δ-T and γ-TE reduced PGE$_2$ formation, even in the presence of sesamin which blocks carboxychromanol formation (FIGS. 1 and 2). 9' and γ-CEHC inhibited COX-2 activity in intact cells where COX-2 was pre-induced and exogenous AA was added. In contrast, these compounds are less effective in enzyme-based assays (Table 1). This selectivity between cellular and enzyme studies resembles scenarios of weak COX inhibitors, e.g. acetaminophen and salicylate, which have been reported to inhibit COX activity in certain cellular environments but are largely in vain in assays with purified enzymes (20, 30, 31). The observed selectivity has been attributed to the difference in lipid hydroperoxide generation (30, 31). Compared with cultured cells where the formation of PGG$_2$ is moderate because of limited induction of the enzyme and AA release, PGG$_2$ is often generated in much higher quantities in assays using purified enzyme (30, 31). Consistently, addition of lipid peroxide, e.g. PGG$_2$, antagonizes inhibitory effect of acetaminophen and salicylate (30, 31). Based on the current study, we conclude that like acetaminophen and salicylate, γ-CEHC and vitamin E forms are weak COX inhibitors, and they may inhibit COX activity only when lipid hydroperoxide is relatively low, e.g. low levels of COX and AA. 9' is also less efficient in enzyme-based assays (Table 1), but its IC50 needs to be further determined.

One important implication of our current findings is that different bioactivity among vitamin E forms may be rooted in their distinct metabolism. To this end, long-chain carboxychromanols may contribute to in vivo anti-inflammatory effect of γ-T (3-2). We and others have demonstrated that γ-T inhibited proinflammatory eicosanoids at the inflammatory site and attenuate inflammation-caused damage in various animal models (14, 33-35). Himmelfard et al. reported that γ-T enriched but not α-T-enriched mixed tocopherol inhibited C-reactive protein and IL-6 in kidney-dialysis patients 36). We recently showed that significant amounts of 13' but not 9' were detected in the plasma and liver after γ-T supplementation (17), although pharmacokinetics of 13' formation needs to be further established. Our preliminary data showed that relatively large amounts of 13' (>100 nmol/g) were found in feces as a result of γ-T supplementation in rats. This suggests that 13', a potent inhibitor of COX and potentially abundant in colon tissues, could also contribute to the anti-cancer effect of mixed tocopherols enriched with γ-T and δ-T on ACF in AOM-induced colon cancer in rodent (Newmark, 2006).

In addition, long-chain carboxychromanols and their analogs may be useful and novel anti-inflammatory agents. We found that besides inhibition of COX-1 and COX-2, 9' and 13' appeared to also inhibit 5-lipoxygenase activity, which is a key enzyme to catalyze generation of pro-inflammatory leukotrienes. Targeting on both COX and lipoxygenase is particularly interesting because inhibition of these multiple pathways can not only result in more potent anti-inflammatory effect, but also reduce potential adverse effect caused by a shunt in arachidonate metabolism to either pathway.

We found that 13'-carboxychromanol (Scheme 4), a long-chain carboxychromanol which is derived from vitamin E, inhibited COX-2 and COX-1 activity with IC50 at low microM (4-7 μM) concentrations, as shown in COX activity assays in intact cells and using purified COX-1 and COX-2. The inhibitory potency is similar to ibuprofen (IC50-5 μM).

Although another metabolite, 9'-COOH, also inhibited COX-2 activity in assays using intact cells, but at up to 20 μM, it did not inhibit COX-1 or COX-2 in the assays using purified COX-1 or COX-2, which indicates that 9'-COOH is a much weaker inhibitor than 13'-COOH. These studies also indicate that the inhibitory potency depends on the length of the side chain (consistently, 3'-COOH is a weaker inhibitor, with an IC50>3000/1 in the enzyme assay).

13'-COOH and 9'-COOH inhibited 5-LOX activity as assayed in HL-60 cells differentiated neutrophils (estimated IC50 is at low microM concentrations).

We previously found that 3'-carboxychromanol inhibited $PGE_2$ and $LTB_4$ at the site of inflammation in a rat's inflammation model (62). Together with the data described above, 13'-carboxychromanol and/or other long-chain carboxychromanols can be much more potent than 3'-carboxychromanol in vivo.

In addition, carboxychromanols are potent antioxidants which may have effect on gene expression of cytokine expression such as TNFα (62).

Taken together, long-chain carboxychromanols are likely useful anti-inflammatory agents because these compounds target multi-pathways which are important to regulation of inflammatory response.

Because sesamin appears to inhibit β-oxidation which metabolizes long-chain carboxychromanols, the addition of sesamin with carboxychromanols will prolong the half life of carboxychromanols, and therefore enhance the effect. Polyphenolic compounds are known to inhibit sulfotransferase activity, which leads to inhibition of sulfation. Our preliminary data indicated that that polyphenols such as curcumin inhibits sulfation of carboxychromanols (sulfated carboxychromanols do not appear to inhibit COX activity). The combination of polyphenols with long-chain carboxychromanols is likely to enhance the efficiency.

As cyclooxygenases and lipoxygenases contribute to cancer development, long-chain carboxychromanols, and their analogs, or their combinations with other bioactive compounds such as sesamin or polyphenolic compounds, are likely to be effective cancer prevention and therapeutic agents. Because chronic inflammation has been implicated in other chronic diseases including cardiovascular diseases, and age-related neurodegenerative diseases, carboxychromanols can be used as therapeutic agents against these diseases.

The description of the present disclosure has been presented for purposes of illustration and description, but is not intended to be exhaustive or limited to embodiments of the disclosure in the form disclosed. Many modifications and variations will be apparent to those of ordinary skill in the art without departing from the scope and spirit of embodiments of the disclosure. The embodiment was chosen and described in order to best explain the principles of embodiments of the disclosure and the practical application, and to enable others of ordinary skill in the art to understand embodiments of the disclosure for various embodiments with various modifications as are suited to the particular use contemplated. Although specific embodiments have been illustrated and described herein, those of ordinary skill in the art appreciate that any arrangement which is calculated to achieve the same purpose may be substituted for the specific embodiments shown and that embodiments of the disclosure have other applications in other environments. This application is intended to cover any adaptations or variations of the present disclosure. The following claims are in no way intended to limit the scope of embodiments of the disclosure to the specific embodiments described herein.

REFERENCES

1. Coussens, L. M. & Werb, Z. (2002) Nature 420, 860-867.
2. Libby, P. (2002) Nature 420, 868-874.
3. Perry, V. H., Cunningham, C., & Holmes, C. (2007) Nat Rev Immunol 7, 161-167.
4. Dubois, R. N., Abramson, S. B., Crofford, L., Gupta, R. A., Simon, L. S., Van DePutte, L. B., & Lipsky, P. E. (1998) FasebJ 12, 1063-1073.
5. Vane, J. R. (1976) Adv Prostaglandin Thromboxane Res 2, 791-801.
6. Vane, J. R., Bakhle, Y. S., & Batting, R. M. (1998) Annu Rev Pharmacol Toxicol 38, 97-120.
7. Vane, J. R. & Bolting, R. M. (1998) Int H Tissue React 20, 3-15.
8. Vane, J. R. & Bolting, R. M. (1998) Ant J ed 104, 2Δ-85; discussion 21 Δ-22S.
9. Gupta, R. A. & Dubois, R. N. (2001) Nat Rev Cancer 1, 11-21.
10. Fulton, A. M., Ma, X., & Kundu, N. (2006) Cancer Res 66, 9794-9797.
11. McLaughlin, P. J. & Weihrauch, J. L. (1979) J Am Diet Assoc 75, 647-665.
12. Jiang, Q., Christen, S., Shigenaga, M. K., & Ames, B. N. (2001) Am J Clin Nutr 74, 714-722.
13. Jiang, Q., Elson-Schwab, I., Courtemanche, C., & Ames, B. N. (2000) Proc Natl Acad Sci USA 97, 11494-11499.
14. Jiang, Q. & Ames, B. N. (2003) Faseb J 17, 816-822.
15. Jiang, Q., Wong, J., Fyrst, H., Saba, J. D., & Ames, B. N. (2004) Proc Natl Acad Sci USA 101, 17825-17830.
16. Birringer, M., Pfluger, P., Kluth, D., Landes, N., & Brigeliub-Flohe, R. (2002) J Nutr 132, 3113-3118.
17. Jiang, Q., Freiser, H., Wood, K. V., & Yin, X. (2007) J Lipid Res 48, 1221-1230.
18. You, C. S., Sontag, T. J., Swanson, J. E., & Parker, R. S. (2005) J Nutr 135, 227232.
19. Sontag, T. J. & Parker, R. S. (2002) J Biol Chem 277, 25290-25296.
20. Mitchell, J. A., Saunders, M., Barnes, P. J., Newton, R., & Belvisi, M. G. (1997) Mol Phannacol 51, 907-912.
21. Parker, R. S., Sontag, T. J., & Swanson, J. E. (2000) Biochem Biophys Res Commun 277, 531-534.
22. McCormick, C. C. & Parker, R. S. (2004) J Nutr 134, 3335-3342.
23. Kurumbail, R. G., Kiefer, J. R., & Mamett, L. J. (2001) CuiT Opin Struct Biol 11, 752-760.
24. Marnett, L. J. & Kalgutkar, A. S. (1999) Trends Pharmacol Sci 20, 465-469.
25. Rieke, C. J., Mulichak, A. M., Garavito, R. M., & Smith, W. L. (1999) J Biol Chem 274, 17109-17114.
26. Bhattacharyya, D. K., Lecomte, M., Rieke, C. J., Garavito, M., & Smith, W. L. (1996) J Biol Chem 271, 2179-2184.

27. Mancini, J. A., Riendeau, D., Falgueyret, J. P., Vickers, P. J., & O'Neill, G. P. (1995) J Biol Chem 270, 29372-29377.
28. Router, C. A. & Mamett, L. J. (2003) Chem Rev 143, 2239-2304.
29. O'Leary, K. A., de Pascual-Tereasa, S., Needs, P. W., Sao, Y. P., O'Brien, N. M., & Williamson, G. (2004) Mutat Res 551, 245-254.
30. Aronoff, D. M., Boutaud, 0., Marnett, L. J., & Oates, J. A. (2003) J Phannacol Exp Ther 304, 589-595.
31. Boutaud, O., Aronoff, D. M., Richardson, J. H., Marnett, L. J., & Oates, J. A. (2002) Proc Nad Acad Sci USA 99, 7130-7135.
32. Reiter, E., Jiang, Q., & Christen, S. (2007) Mol Aspects Med January 11; [Epub ahead of print].
33. Jiang, Q., Lykkesfeldt, J., Shigenaga, M. K., Shigeno, E. T., Christen, S., & Ames, B. N. (2002) Free Radic Brat Med 33, 1534-1542.
34. Takahashi, K., Komaru, T., Takeda, S., Takeda, M., Koshida, R., Nakayama, M., Kokusho, Y., Kawakami, Y., Yamaguchi, N., Miyazawa, T., et at. (2006) J Mol Cell Cardiol 41, 544-554.
35. Yoshida, E., Watanabe, T., Takata, J., Yamazaki, A., Karube, Y., & Kobayashi, S. (2006) J Invest Dermatol 126, 1533-1640.
36. Himmelfarb, J., Kane, J., McMonagle, E., Zaltas, E., Bobzin, S., Boddupalli, S., Phinney, S., & Miller, G. (2003) Kidney Int 64, 978-991.
37. Belardelli, F. (1995) Role of interferons and other cytokines in the regulation of the immune response. Apmis 103, 161-179.
38. Vane, J. R. (1976) Prostaglandins as mediators of inflammation. Adv Prostaglandin Thromboxane Res 2, 791-801.
39. Yokomizo, T., Izumi, T., and Shimizu, T. (2001) Leukotriene B4: metabolism and signal transduction. Arch Biochem Biophys 385, 231-241.
40. McGeer, P. L., and McGeer, E. G. (2001) Inflammation, autotoxicity and Alzheimer disease. Neurobiol Aging 22, 799-809.
41. Libby, P., Ridker, P. M., and Maseri, A. (2002) Inflammation and atherosclerosis. Circulation 105, 1135-1143.
42. Balkwill, F., and Mantovani, A. (2001) Inflammation and cancer: back to Virchow? Lancet 357, 539-545.
43. Samad, T. A., Moore, K. A., Sapirstein, A., Billet, S., Allchorne, A., Poole, S., Bonventre, J. V., and Woolf, C. J. (2001) Interleukin-1beta-mediated induction of Cox-2 in the CNS contributes to inflammatory pain hypersensitivity. Nature 410, 471-475.
44. Williams, J. A., and Shacter, E. (1997) Regulation of macrophage cytokine production by prostaglandin E2. Distinct roles of cyclooxygenase-1 and -2. J Biol Chem 272, 25693-25699.
45. Vane, J. R., Bakhlc, Y. S., and Botting, R. M. (1998) Cyclooxygenases 1 and 2. Annu Rev Pharmacol Toxicol 38, 97-120.
46. Vane, J. R., and Botting, R. M. (1998) Mechanism of action of antiinflammatory drugs. Int J Tissue React 20, 3-15.
47. Mazzon, E., Sautebin, L., Caputi, A. P., and Cuzzocrea, S. (2006) 5-lipoxygenase modulates the alteration of paracellular barrier function in mice ileum during experimental colitis. Shock 25, 377-383.
48. van den Berg, W. B. (2001) Uncoupling of inflammatory and destructive mechanisms in arthritis. Semin Arthritis Rheum 30, 7-16.
49. van den Berg, W. B. (2001) Anti-cytokine therapy in chronic destructive arthritis. Arthritis Res 3, 18-26.
50. Lorenz, H. M., and Kalden, J. R. (2002) Perspectives for TNF-alpha-targeting therapies. Arthritis Res 4, S 17-24.
51. Yoshimura, R., Sano, H., Masuda, C., Kawamura, M., Tsubouchi, Y., Chargui, J., Yoshimura, N., Hla, T., and Wada, S. (2000) Expression of cyclooxygenase-2 in prostate carcinoma. Cancer 89, 589-596.
52. Levy, G. N. (1997) Prostaglandin H synthases, non-steroidal anti-inflammatory drugs, and colon cancer. Faseb./11, 234-247.
53. Kurie, J. M., and Dubois, R. N. (2001) Prostaglandin E synthase: another enzyme in the cyclooxygenase pathway driving epithelial cancer? Clin Cancer Res 7, 2608-2610.
54. Gupta, S., Srivastava, M., Ahmad, N., Sakamoto, K., Bostwick, D. G., and Mukhtar, H. (2001) Lipoxygenase-5 is overexpressed in prostate adenocarcinoma. Cancer 91, 737-743.
55. Giovannucci, E., Egan, K. M., Hunter, D. J., Stampfer, M. J., Colditz, G. A., Willett, W. C., and Speizer, F. E. (1995) Aspirin and the risk of colorectal cancer in women [see comments]. N Engl J Med 333, 609-614.
56. Smalley, W. E., and DuBois, R. N. (1997) Colorectal cancer and nonsteroidal anti-inflammatory drugs. Adv Pharmacol 39, 1-20.
57. Thun, M. J., Namboodiri, M. M., Calle, E. E., Flanders, W. D., and Heath, C. W., Jr. (1993) Aspirin use and risk of fatal cancer [see comments]. Cancer Res 53, 1322-1327.
58. Feuerstein, G., and Hallenbeck, J. M. (1987) Leukotrienes in health and disease. Faseb J 1, 186-192.
59. Schonbeck, U., Sukhova, G. K., Graber, P., Coulter, S., and Libby, P. (1999) Augmented expression of cyclooxygenase-2 in human atherosclerotic lesions. Am J Pathol 155, 1281-1291.
60. Wynne, H. A., and Campbell, M. (1993) Pharmacoeconomics of nonsteroidal anti-inflammatory drugs (NSAIDs). Pharmacoeconomics 3, 107-123.
61. Gupta, R. A., and Dubois, R. N. (2001) Colorectal cancer prevention and treatment by inhibition of cyclooxygenase-2. Nature reviews 1, 11-21.
62. Jiang, Q., and Ames, B. N. (2003) Gamma-tocopherol, but not alpha-tocopherol, decreases proinflammatory eicosanoids and inflammation damage in rats. Faseb J 17, 816-822.
63. Wang, D., and Dubois, R. N. (2010) Eicosanoids and cancer. Nature reviews. Cancer 10, 181-193.
64. Marks, F., Muller-Decker, K., and Furstenberger, G. (2000) A causal relationship between unscheduled eicosanoid signaling and tumor development: cancer chemoprevention by inhibitors of arachidonic acid metabolism. Toxicology 153, 11-26.
65. Marnett, L. J. (1992) Aspirin and the potential role of prostaglandins in colon cancer. Cancer Res 52, 5575-5589.
66. Rainsford, K. D. (2001) The ever-emerging anti-inflammatories. Have there been any real advances? J Physiol Paris 95, 11-19.
67. Jiang, Q., Yin, X., Lill, M. A., Danielson, M. L., Freiser, H., and Huang, J. (2008) Long-chain carboxychromanols, metabolites of vitamin E, are potent inhibitors of cyclooxygenases. Proceedings of the National Academy of Sciences of the United States of America 105, 20464-20469.
68. Cho, Y. S., Kim, H. S., Kim, C. H., and Cheon, H. G. (2006) Application of the ferrous oxidation-xylenol orange assay for the screening of 5-lipoxygenase inhibitors. Analytical biochemistry 351, 62-68.

69. Jiang, Z., Yin, X., and Jiang, Q. (2011) Natural forms of vitamin E and 13'-carboxychromanol, a long-chain vitamin E metabolite, inhibit leukotriene generation from stimulated neutrophils by blocking calcium influx and suppressing 5-lipoxygenase activity, respectively. J Immunology 186, 1173-1179.

70. Nakamura, T., Aoyama, Y., Fujita, T., and Katsui, G. (1975) Studies on tocopherol derivatives: V. Intestinal absorption of several d,l-3,4-3H2-alpha-tocopherol esters in the rat. Lipids 10, 627-633.

71. Brisson, L., Castan, S., Fontbonne, H., Nicoletti, C., Puigserver, A., and Ajandouz el, H. (2008) Alpha-tocopheryl acetate is absorbed and hydrolyzed by Caco-2 cells comparative studies with alpha-tocopherol. Chemistry and physics of lipids 154, 33-37.

The invention claimed is:

1. A pharmaceutical composition comprising a conjugated 13'-carboxychromanol compound

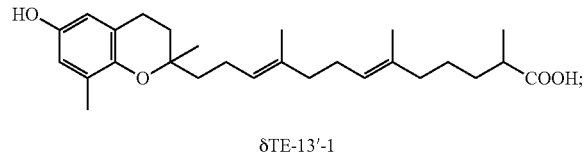 [SMILES: C/C(=C\CCC1(C)CCc2cc(O)cc(C)c2O1)CC/C=C(\C)CCCC(C)C(=O)O]

δTE-13'-1 and
a pharmaceutically acceptable polyphenolic sulfation inhibitor, wherein the polyphenolic sulfation inhibitor is sesamin or curcumin.

2. A method for treating a physiological disorder associated with inflammation in the gut, the method comprising administering a therapeutic amount of a conjugated 13'-carboxychromanol compound:

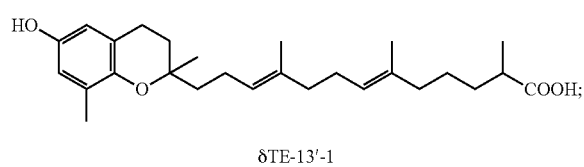 [SMILES: C/C(=C\CCC1(C)CCc2cc(O)cc(C)c2O1)CC/C=C(\C)CCCC(C)C(=O)O]

δTE-13'-1 and
a pharmaceutically acceptable polyphenolic sulfation inhibitor, wherein the polyphenolic sulfation inhibitor is sesamin or curcumin.

3. The method of claim 2, wherein said physiological disorder is selected from the group consisting of inflammatory bowel disease, gastritis, irritable bowel syndrome, ulcerative colitis, Crohn's disease, and diarrhea.

4. The method of claim 2, wherein said patient is a human.

5. The method of claim 2, wherein the sufficient amount is from about 5 uM to about 20 uM.

* * * * *